United States Patent
Bicocca et al.

(10) Patent No.: US 12,098,364 B2
(45) Date of Patent: *Sep. 24, 2024

(54) METHODS AND COMPOSITIONS FOR COLLECTION AND PRESERVATION OF BIOLOGICALS

(71) Applicant: Convergent Genomics, Inc., South San Francisco, CA (US)

(72) Inventors: Vincent T. Bicocca, South San Francisco, CA (US); Trevor Gilpin Levin, South San Francisco, CA (US)

(73) Assignee: Convergent Genomics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/888,409

(22) Filed: Aug. 15, 2022

(65) Prior Publication Data
US 2022/0389405 A1  Dec. 8, 2022

Related U.S. Application Data

(63) Continuation of application No. 17/225,006, filed on Apr. 7, 2021, now Pat. No. 11,421,217.

(51) Int. Cl.
*C12N 15/10* (2006.01)
*C12Q 1/6806* (2018.01)

(52) U.S. Cl.
CPC ....... *C12N 15/1013* (2013.01); *C12Q 1/6806* (2013.01)

(58) Field of Classification Search
CPC .......................... C12Q 1/6806; C12N 15/1013
See application file for complete search history.

(56) References Cited

U.S. PATENT DOCUMENTS

| 7,527,929 | B2 | 5/2009 | McKernan et al. |
| 8,877,436 | B2 | 11/2014 | Eder et al. |
| 11,421,217 | B1 * | 8/2022 | Bicocca ............... C12Q 1/6806 |
| 2010/0105060 | A1 | 4/2010 | Eder et al. |

FOREIGN PATENT DOCUMENTS

WO    WO 2020/023630 A1    1/2020

OTHER PUBLICATIONS

Thermo Scientific Sera-Mag SpeedBeads, Carboxiate-Modified Magnetic Particles, Product Specifications (2010), 2 pages, Thermo Fisher Scientific, Inc.

* cited by examiner

*Primary Examiner* — Jezia Riley
(74) *Attorney, Agent, or Firm* — DLA Piper LLP (US)

(57) ABSTRACT

Provided herein are compositions and methods of use thereof for collection, preservation and/or extraction of biologicals from a subject. For example, a solution that enables collection, preservation, and extraction of nucleic acids in a single step, and methods of using such solution are provided. In some embodiments, the compositions, kits, and methods are useful for the collection and analysis of samples from patients that have or are suspected of having SARS-CoV-2 virus that can cause Covid-19.

21 Claims, 5 Drawing Sheets

METHODS AND COMPOSITIONS FOR COLLECTION AND PRESERVATION OF BIOLOGICALS

CROSS-REFERENCE TO RELATED APPLICATIONS

This application is a continuation application of U.S. application Ser. No. 17/225,006 filed Apr. 7, 2021, now issued as U.S. Pat. No. 11,421,217. The disclosure of the prior application is considered part of and is incorporated by reference in the disclosure of this application.

BACKGROUND OF THE INVENTION

PCT Patent Application No. WO/2020/023630 discloses "a preservation mixture comprising an iron chelator, wherein the preservation mixture is configured to preserve nucleic acid molecules in a urine sample and prevent growth of microbes in the sample."

U.S. Pat. No. 8,470,536 discloses "compositions and methods for isolation and storage of nucleic acids from bodily fluids, such as saliva, for detection of nucleotide sequences. More specifically, the invention relates to compositions and methods that do not require a separate step for extraction of nucleic acids prior to use in nucleic acid amplification reactions."

US Patent Application No. US20190062806 discloses "compositions for preserving, stabilizing, and/or preparing nucleic acid in a biological sample." US Patent Application No. 20150218653 discloses "a kit . . . comprising: a) magnetic particles, wherein the surface of the magnetic particles comprise anion exchange moieties; b) a denaturation agent which is an alkaline solution comprising a base, preferably NaOH or KOH; and c) a composition comprising a chaotropic agent and optionally one or more additives selected from the group of chelating agents, buffering agents and preservatives."

SUMMARY OF THE INVENTION

The instant disclosure is based, at least in part, on the discovery of solutions for collecting/storing nucleic acids that improve stability of nucleic acids. Further, the disclosure is also based, in part, on the discovery that nucleic acids from a biological sample can be preserved and extracted using a single solution. In various aspects and embodiments, the disclosure may relate to a nucleic acid enhanced preservation media with integrated extraction steps.

In illustrative embodiments, the disclosure provides embodiments 1-171 noted below.

DETAILED DESCRIPTION OF THE INVENTION

The instant disclosure is based, at least in part, on the discovery of solutions for collecting/storing nucleic acids that improve stability of nucleic acids. Further, the disclosure is also based, in part, on the discovery that nucleic acids from a biological sample can be preserved and extracted using a single solution. In various aspects and embodiments, the disclosure may relate to a nucleic acid enhanced preservation media with integrated extraction steps. Due the unstable nature of cell-free nucleic acids, accurate and reproducible screening can be difficult with existing sample preservation solutions, thus in some embodiments the disclosure relates to solutions that have improved properties with regard to stability of nucleic acid during storage. In various embodiments, the disclosure may relate to methods that involve collecting a biological sample from a subject, contacting the sample with a preservation media such as described herein, extracting nucleic acids from the sample using magnetic beads, and isolating those beads for downstream analysis.

In some embodiments, the solutions, kits and methods provided herein may be useful for collecting, storing and/or extracting samples that have, or may have, nucleic acid. In some embodiments, the solutions, kits and methods may be useful for collecting, storing and/or extracting samples that have, are suspected of having, or at risk of having nucleic acid, for example, nucleic acid from a pathogen. In this regard, the solutions, kits, and methods may in certain embodiments reduce the "false negative" rate of assays and diagnostics designed to detect pathogen nucleic acid in a sample. Importantly, in 2019, 2020, and perhaps later, the world has been victim of a severe COVID-19 pandemic caused by the RNA-based SARS-CoV-2 virus. One of the challenges of attempts to reign in the COVID-19 has been to establish effective tests and diagnostics for detecting SARS-CoV-2 RNA in samples collected from subjects that have or may have the virus. These challenges are brought about, at least in part, by the difficulty to collect, store, and transport samples without resulting in the degradation of the viral RNA. Viral RNA degradation during collection, storage, and/or transport can result in false-negative test results in the subsequent nucleic acid evaluation methods (e.g., PCR, NexGen sequencing, etc.) that, in turn, can result in further spread of the virus in populations around the world. Thus, in certain aspects and embodiments the present disclosure is intended to provide solutions, kits, and methods that improve the ability to collect, store, and transport samples having nucleic acid (such as SARS-CoV-2 RNA), such that the nucleic acid remains sufficiently stable for subsequent analysis. Another challenge in COVID-19 testing arose from the fact that the pandemic resulted in a dramatic increase in the world-wide demand for nucleic acid-based diagnostics as well as the volume of samples being processed and evaluated daily. Thus, it is an additional objective of some of the embodiments of the present disclosure to increase the efficiency and lower the cost of nucleic acid diagnostics. Generally, in the process of nucleic acid preservation and extraction, one solution is used for the preservation, storage and/or transport of a nucleic acid and a separate solution is used to extract the nucleic acids from sample—this two-solution process can often involve an increase in cost and labor required. Along these lines, some of the embodiments of solutions, kits, and methods provided herein allow for nucleic acid (such as SARS-CoV2 RNA) to be stably preserved and extracted from a sample using a single preservation/extraction solution. In some embodiments of the solutions, kits, and methods presented herein, paramagnetic beads present in a solution of the disclosure bind nucleic acids from a sample and can facilitate nucleic acid extraction. Further, certain embodiments of the solutions, kits, and methods provided herein are particularly useful in high-throughput nucleic acid processing and evaluation. In some embodiments, the ability to use a single solution for sample collection and extraction allows for all of the sample (and its nucleic acid) to be subjected to nucleic acid analysis—such embodiments may increase the amount of tested nucleic acid, and in turn, increasing analysis sensitivity.

As used herein, the term "nucleic acid" refers to polynucleotides such as deoxyribonucleic acid (DNA) or ribonucleic acid (RNA). Nucleic acids include but are not limited to genomic DNA, cDNA, mRNA, iRNA, miRNA, tRNA, ncRNA, rRNA, aptamers, plasmids, anti-sense DNA strands, shRNA, ribozymes, nucleic acids conjugated and oligonucleotides. Nucleic acid of the disclosure may be naturally occurring or recombinantly produced or chemically synthesized. Nucleic acid may be present as a single-stranded or double-stranded and linear or covalently circularly closed molecule.

Accordingly, in a first aspect, provided is a solution that includes a chelating agent, a detergent, a salt, a cationic polymer and a pH buffering agent. In some embodiments, a solution as provided herein includes a first and second chelating agent, a first and second detergent, a salt, a cationic polymer and a pH buffering agent. In some embodiments, the solution further includes paramagnetic beads. In some embodiments the solution further includes an antimicrobial. In some embodiments, a solution of the disclosure includes a chelating agent, a detergent, a salt, a cationic polymer, a pH buffering agent, a crowding agent and paramagnetic beads. In some embodiments, the solution includes a chelating agent, a detergent, a salt, a cationic polymer, a pH buffering agent and an antimicrobial. In some embodiments, a solution is provided that includes (1) a chelating agent (or two or more chelating agents), (2) a detergent (or two or more detergents), (3) a salt, (4) a cationic polymer, (5) a pH buffering agent, (6) a crowding agent, (7) paramagnetic beads and (8) an antimicrobial.

In some embodiments, the solution of any one of the aspects or embodiments provided herein includes one or more chelating agents. In some embodiments, the chelating agent[s] is configured to preserve nucleic acid molecules in a sample and prevent growth of microbes in the sample. In some embodiments, the chelating agent is an iron chelator. In some embodiments, the solution of any one of the aspects or embodiments provided herein includes one or more chelating agents selected from the group consisting of enterobactin, deferasirox (DFS), deferiprone (DFP), deferoxamine mesylate (DFM), EDTA, and EGTA. In some embodiments, the solution of any one of the aspects or embodiments provided herein includes enterobactin as a chelating agent. In some embodiments, the solution of any one of the aspects or embodiments provided herein includes deferasirox as a chelating agent. In some embodiments, the solution of any one of the aspects or embodiments provided herein includes deferiprone as a chelating agent.

In some embodiments, the solution of any one of the aspects or embodiments provided herein includes deferoxamine mesylate as a chelating agent. In some embodiments, the solution of any one of the aspects or embodiments provided herein includes EDTA as a chelating agent. In some embodiments, the solution of any one of the aspects or embodiments provided herein includes EGTA as a chelating agent. In some embodiments the solution includes a first and second chelating agent (where agents are described herein as a first and second of a class of agent, it is inferred that the first agent and second agent are different). In some embodiments, the solution of any one of the aspects or embodiments provided herein includes two or more chelating agents selected from the group consisting of enterobactin, deferasirox (DFS), deferiprone (DFP), deferoxamine mesylate (DFM), EDTA, and EGTA. In some embodiments, the solution of any of the aspects and embodiments provided herein includes a chelating agent present in the solution in an amount that is between 25-750 µM. In some embodiments, the solution of any of the aspects and embodiments provided herein includes a chelating agent that is between 1-1,000 µM; or 10-50 µM; or 50-100 µM; or 100-200 µM; 100-150 µm; or 200-300 µM; or 300-400 µM; or 400-500 µM; or 500-600 µM; or 600-700 µM; or 700-800 µM; or 800-900 µM; or 900-1000 µM; or 50-250 µM; or 100-150 µM; or 50-600 µM; or 100-500 µM; or about 70 µM; or about 75 µM; or about 80 µM; or about 90 µM; or about 100 µM; or about 110 µM; or about 120 µM; or about 125 µM; or about 130 µM; or about 140 µM; or about 150 µM; or about 175 µM; or about 200 µM; or about 250 µM; or about 300 µM; or about 400 µM; or about 500 µM in the solution. In some embodiments, the solution of any of the aspects and embodiments provided herein includes a chelating agent that is between 1-100 mM in the solution. In some embodiments, the solution of any of the aspects and embodiments provided herein includes a chelating agent that is between 1-1,000 mM; or 10-50 mM; or 50-100 mM; or 100-200 mM; or 25-75 mM; or 50-55 mM; or 55-60 mM; or 60-65 mM; or 65-70 mM; or 70-75 mM; or 75-80 mM; or 85-90 mM; or 90-95 mM; or 95-100 mM; or 100-125 mM; or 125-150 mM; or about 10 mM; or about 25 mM; or about 50 mM; or about 52.5 mM; or about 55 mM; or about 57.5 mM; or about 60 mM; or about 62.5 mM; or about 65 mM; or about 67.5 mM; or about 70 mM; or about 72.5 mM; or about 75 mM; or about 77.5 mM; or about 80 mM; or about 85 mM; or about 90 mM; or about 95 mM; or about 100 mM; or about 125 mM or about 150 mM; or about 175 mM; or about 200 mM in the solution. In some embodiments, a solution as provided herein includes a first chelating agent and a second chelating agent; wherein the first chelating agent is present in an amount that is 1-1,000 µM; or 10-50 µM; or 50-100 µM; or 100-200 µM; 100-150 µm; or 200-300 µM; or 300-400 µM; or 400-500 µM; or 500-600 µM; or 600-700 µM; or 700-800 µM; or 800-900 µM; or 900-1000 µM; or 50-600 µM; or 100-500 µM; or about 70 µM; or about 75 µM; or about 80 µM; or about 90 µM; or about 100 µM; or about 110 µM; or about 120 µM; or about 125 µM; or about 130 µM; or about 140 µM; or about 150 µM; or about 175 µM; or about 200 µM; or about 250 µM; or about 300 µM; or about 400 µM; or about 500 µM in the solution; and the second chelating agent is present in an amount that is 1-1,000 mM; or 10-50 mM; or 50-100 mM; or 100-200 mM; or 25-75 mM; or 50-55 mM; or 55-60 mM; or 60-65 mM; or 65-70 mM; or 70-75 mM; or 75-80 mM; or 85-90 mM; or 90-95 mM; or 95-100 mM; or 100-125 mM; or 125-150 mM; or about 10 mM; or about 25 mM; or about 50 mM; or about 52.5 mM; or about 55 mM; or about 57.5 mM; or about 60 mM; or about 62.5 mM; or about 65 mM; or about 67.5 mM; or about 70 mM; or about 72.5 mM; or about 75 mM; or about 77.5 mM; or about 80 mM; or about 85 mM; or about 90 mM; or about 95 mM; or about 100 mM; or about 125 mM or about 150 mM; or about 175 mM; or about 200 mM in the solution. In some embodiments of the solutions provided herein, the solution includes EDTA as a chelating agent; wherein the EDTA is present in the solution in an amount that is 1-1,000 mM; or 10-50 mM; or 50-100 mM; or 100-200 mM; or 25-75 mM; or 50-55 mM; or 55-60 mM; or 60-65 mM; or 65-70 mM; or 70-75 mM; or 75-80 mM; or 85-90 mM; or 90-95 mM; or 95-100 mM; or 100-125 mM; or 125-150 mM; or 55-75 mM; or about 10 mM; or about 25 mM; or about 50 mM; or about 52.5 mM; or about 55 mM; or about 57.5 mM; or about 60 mM; or about 62.5 mM; or about 65 mM; or about 67.5 mM; or about 70 mM; or about 72.5 mM; or about 75 mM; or about 77.5 mM; or about 80 mM; or about 85 mM; or about 90 mM; or about 95 mM; or about 100 mM; or about 125 mM or about 150 mM; or about 175 mM; or about 200 mM in the solution. In some embodiments of the solutions provided herein, the solution includes DFM as a chelating agent;

wherein the DFM is present in the solution in an amount that is 1-1,000 µM; or 10-50 µM; or 50-100 µM; or 100-200 µM; 100-150 µm; or 200-300 µM; or 300-400 µM; or 400-500 µM; or 500-600 µM; or 600-700 µM; or 700-800 µM; or 800-900 µM; or 900-1000 µM; or 50-600 µM; or 100-500 µM; or about 70 µM; or about 75 µM; or about 80 µM; or about 90 µM; or about 100 µM; or about 110 µM; or about 120 µM; or about 125 µM; or about 130 µM; or about 140 µM; or about 150 µM; or about 175 µM; or about 200 µM; or about 250 µM; or about 300 µM; or about 400 µM; or about 500 µM in the solution. In some embodiments, the first chelator has a first binding affinity for a first metal and the second chelator has a second binding affinity for the first metal, the first binding affinity being greater than the second binding affinity. In some embodiments, the first metal comprises one or more member(s) selected from the group consisting of: vanadium (V), chromium (Cr), manganese (Mn), iron (Fe), cobalt (Co), copper (Cu), zinc (Zn), and molybdenum (Mo). In some embodiments, the first chelator has a third binding affinity for a second metal and the second chelator has a fourth binding affinity for the second metal, the second metal being different from the first metal, and the third binding affinity being less than the fourth binding affinity. In some embodiments, the first chelator comprises one or more member(s) selected from the group consisting of: a siderophore, a nucleoside monophosphate, a nucleoside diphosphate, a nucleoside triphosphate, and a functional variant thereof. In some embodiments, the siderophore comprises one or more member(s) selected from the group consisting of: Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Deferoxamine Mesylate, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Tel, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopropen, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriomicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin 51, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin. In some embodiments, the second chelator comprises one or more member(s) selected from the group consisting of: ethylenediaminetetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N'''-hexaacetic acid (TTHA), dihydroxyethylglycine (DHEG), iminodiacetic acid (IDA), nitrilotrimethylphosphonic acid (NTP), N-(2-hydroxyethyl) iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) and 1,2-bis(o-aminophenoxy)ethane-N,N,N',N'-tetraacetic acid (BAPTA).

In some embodiments, a solution of the disclosure includes a detergent wherein the detergent is one or more selected from the group consisting of cholate, deoxycholate, sodium dodecyl sulfate, sarkosyl, DDM, digitonin, NP-40, Triton X-100, Tween 20, and Tween 80. In some embodiments, a solution of any of the aspects and embodiments provided herein includes a detergent wherein the detergent is cholate. In some embodiments, a solution of any of the aspects and embodiments provided herein includes a detergent wherein the detergent is deoxycholate. In some embodiments, a solution of any of the aspects and embodiments provided herein includes a detergent wherein the detergent is sodium dodecyl sulfate. In some embodiments, a solution of any of the aspects and embodiments provided herein includes a detergent wherein the detergent is sarkosyl. In some embodiments, a solution of any of the aspects and embodiments provided herein includes a detergent wherein the detergent is DDM. In some embodiments, a solution of any of the aspects and embodiments provided herein includes a detergent wherein the detergent is digitonin. In some embodiments, a solution of any of the aspects and embodiments provided herein includes a detergent wherein the detergent is NP-40. In some embodiments, a solution of any of the aspects and embodiments provided herein includes a detergent wherein the detergent is Triton X-100 (2-[4,4-trimethylpentan-2-yl)phenoxy]ethanol). In some embodiments, a solution of any of the aspects and embodiments provided herein includes a detergent wherein the detergent is Tween 20. In some embodiments, a solution of any of the aspects and embodiments provided herein includes a detergent wherein the detergent is Tween 80. In some embodiments the detergent is present in the solution in an amount that is 0.1-1.0%; or about 0.1-0.5%; or about 0.5-1.0%; or 0.2-0.8%; or 0.3-0.7%; or 0.4-0.6%; or about 0.1%; or about 0.2%; or about 0.3%; or about 0.4%; or about 0.5%; or about 0.6%; or about 0.7%; or about 0.8%; or about 0.9%; or about 1.0% weight/volume of the solution. In some embodiments the total amount of one or more detergents is present in the solution in an amount that is 0.1-1.0%; or about 0.1-0.5%; or about 0.5-1.0%; or 0.2-0.8%; or 0.3-0.7%; or 0.4-0.6%; 0.1-2.0%; or about 0.5-0.1.5%; or about 0.75-1.25%; or about 0.1%; or about 0.2%; or about 0.3%; or about 0.4%; or about 0.5%; or about 0.6%; or about 0.7%; or about 0.8%; or about 0.9%; or about 1.0%; or about 1.1%; or about 1.2%; or about 1.25%; or about 1.3%; or about 1.4%; or about 1.5%; or about 1.6%; or about 1.7%; or about 1.75%; or about 1.8%; or about 1.9%; or about 2% weight/volume of the solution. In some embodiments, a solution of any of the aspects and embodiments provided herein includes cholate in an amount between 0.1-0.5%; or about 0.1% or about 0.2%; or about 0.3%; or about 0.4%; or about 0.5% weight/volume of the solution. In some embodiments, a solution of any of the aspects and embodiments provided herein includes Deoxycholate in an amount between 0.1-0.5%; or about 0.1%; or about 0.2%; or about 0.3%; or about 0.4%; or about 0.5% weight/volume of the solution. In some embodiments, a solution of any of the aspects and embodiments provided herein includes Sodium Dodecyl Sulfate (SDS) in an amount between 0.1-1.0%; or about 0.1-0.5%; or about 0.5-1.0%; or 0.2-0.8%; or 0.3-0.7%; or 0.4-0.6%; or about 0.1%; or about 0.2%; or about 0.3%; or about 0.4%; or about 0.5%; or about 0.6%; or about 0.7%; or about 0.8%; or about 0.9%; or about 1.0% weight/volume of the solution. In some embodiments, a solution of any of the aspects and embodiments provided herein includes Sarkosyl in an amount between 0.05-0.5%; or 0.05-0.1%; or 0.075-0.125%; or 0.2-0.4%; or about 0.05%; or about 0.1%; or about 0.2%; or about 0.3%; or about 0.4%; or about 0.5% weight/volume of the solution. In some embodiments, a solution of any of the aspects and embodiments provided herein includes DDM in an amount between 0.1-1.0%; or 0.2-1.0%; or about 0.1-0.5%; or about 0.5-1.0%; or 0.3-0.7%; or 0.4-0.6%; or about 0.1%; or about 0.2%; or about 0.3%; or about 0.4%; or about 0.5%; or about 0.6%; or about 0.7%; or about 0.8%; or about 0.9%; or about 1.0% weight/volume of the solution. In some embodiments, a solution of any of the aspects and embodiments provided herein includes digitonin in an amount between 0.2-2.0%; or 0.2-1.0%; or 0.3-0.7%; or 0.18-1.2%; or 0.5-1.5%; or 1.0-2.0%; or about 0.2%; 0.3%; or about 0.4%; or about 0.5%; or about 0.6%; or about 0.7%; or about 0.8%; or about 0.9%; or about 1.0%; or about 1.2%; or about 1.5%; or about 1.8%; or about 2% weight/volume of the solution. In some embodiments, a solution of any of the aspects and embodiments provided herein includes NP-40 in an amount between 0.05-1.0%; or 0.05-0.1%; or 0.075-0.125%; or 0.2-0.4%; 0.1-0.5%; or about 0.5-1.0%; or 0.3-0.6%; or about 0.05%; or about 0.1%; or about 0.2%; or about 0.3%; or about 0.4%; or about 0.5%; or about 0.7%; or about 0.8%; or about 0.9%; or about 1.0% weight/volume of the solution. In some embodiments, a solution of any of the aspects and embodiments provided herein includes Triton X-100 in an amount between 0.1-1.0%; or about 0.1-0.5%; or about 0.5-1.0%; or 0.2-0.8%; or 0.3-0.7%; or 0.4-0.6%; or about 0.1%; or about 0.2%; or about 0.3%; or about 0.4%; or about 0.5%; or about 0.6%; or about 0.7%; or about 0.8%; or about 0.9%; or about 1.0% weight/volume of the solution. In some embodiments, a solution of any of the aspects and embodiments provided herein includes Tween 20 in an amount between 0.05-0.5%; or 0.05-0.1%; or 0.075-0.125%; or 0.2-0.4%; or about 0.05%; or about 0.1%; or about 0.2%; or about 0.3%; or about 0.4%; or about 0.5% weight/volume of the solution. In some embodiments, a solution of any of the aspects and embodiments provided herein includes Tween 80 in an amount between 0.05-0.5%; or 0.05-0.1%; or 0.075-0.125%; or 0.2-0.4%; or about 0.05%; or about 0.1%; or about 0.2%; or about 0.3%; or about 0.4%; or about 0.5% weight/volume of the solution. In some embodiments, a solution as provided herein includes two or more detergents, for example a first detergent and a second detergent. In some embodiments, a solution as provided herein includes a first and second detergent wherein the first and second detergent combined are present in the solution in an amount that is 0.01-5%; or 0.1-0.5%; or 0.05%-0.1%; or 0.1%-0.5%; or 0.5%-1%; or 1%-2%; or 2%-3%; or 3%-4%; or 4%-5%; or 0.04-0.06%; or 0.08-0.12%; or 0.13-0.17%; or 0.3-0.7%; or 0.75-1.25%; or 1-3%; or about 0.01%; or about 0.025%; or about 0.05%; or about 0.075%; or about 0.1%; or about 0.25%; or about 0.5%; or about 0.75%; or about 1%; or about 1.25%; or about 1.5%, or about 2%; or about 3%; or about 4%; or about 5% weight/volume. In some embodiments having one or more detergents as provided herein, the cumulative amounts of the one or more detergents that are present in the solution are present in an amount that is 0.01-5%; or 0.1-0.5%; or 0.05-0.1%; or 0.1-0.5%; or 0.5-1%; or 1-2%; or 2-3%; or 3%4%; or 4-5%; or 0.04-0.06%; or 0.08-0.12%; or 0.13-0.17%; or 0.3-0.7%; or 0.75-1.25%; or 0.5-1.5%; or 1-3%; or about 0.01%; or about 0.025%; or about 0.05%; or about 0.075%; or about 0.1%; or about 0.25%; or about 0.5%; or about 0.75%; or about 1%; or about 1.25%; or about 1.5%, or about 2%; or about 3%; or about 4%; or about 5% weight/volume. In certain embodiments the solutions as provided herein include a first detergent and a second detergent; wherein one detergent is an ionic detergent and one detergent is a non-ionic detergent. In some embodiments, a combination of ionic and non-ionic detergents can create an emulsion that is insensitive to temperature changes and/or confers solubility properties that do not exist with either detergent alone. These detergent emulsions can in some embodiments facilitate the lysis step of nucleic acid extraction by disrupting membranes. In previous nucleic acid extraction solutions, a single ionic or non-ionic detergent is used to facilitate lysis or extraction, but it will generally be done in an extraction procedure that is step-wise and separates (1) sample collection from (2) lysis, (3) nucleic acid extraction, and (4) washing of precipitated nucleic acid. To enable the integration of steps 1, 2, and 3 requires a specific combination of two detergents of differing physical characteristics; in some embodiments of the solutions of the present disclosure one detergent is ionic and the other is non-ionic. In solutions that include only an ionic detergent (without a non-ionic detergent), the detergent may precipitation from solution through crystal formation; render the solution ineffective. In solutions that include only a nonionic detergent (without an ionic detergent) the detergent may also precipitate from solution, and greater detergent concentration would be required to inactivate pathogen and facilitate lysis and extraction. Attempts to increase the concentration of the nonionic detergent may be ineffective as it would only increase the rate of precipitation from solution.

In certain embodiments, a solution of the disclosure includes a pH buffering agent (i.e., a pH buffer). pH buffers are well known in the art and are generally used to maintain solution at or near a particular pH value. In certain embodiments one of ordinary skill in the art is capable of creating a suitable pH buffer system that is suitable for a solution of the present disclosure. For instance, in some embodiments the pH buffer may maintain the solution of the disclosure at a pH of at least about 7, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0, or more. In some embodiments the pH buffer may maintain the solution at a pH of at most about 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, or 7.0, or less. The pH buffer may maintain the preservation solution at a pH that is within a range defined by any two of the preceding values. For instance, in certain embodiments the pH buffer may maintain the preservation solution at a pH that is 7-9; or 7-8; or 6-8; or 6-7; or 6.5-7.5; 6.75-7.25; or 7.25-7.75; or 7.5-8.5; or 7.75-8.25; or 8-9; or 8.25-8.75; or about 7.1; or about 7.2; or about 7.3; or about 7.4; or about 7.5; or about 7.6; or about 7.7; or about 7.8; or about 7.9; or about 8.0; or about 8.1, 8.2; or about 8.3; or about 8.4; or about 8.5; or about 8.6; or about 8.7; or about 8.8; or about 8.9; or about; or about 9.0. The pH buffer may in some embodiments maintain the preservation solution at a pH of about 8. In some embodiments, a buffering agent is present in the solution in an amount that is 25-250 mM; or 50-200 mM; or 75-175 mM; or 100-150 mM; or about 75 mM; or about 100 mM; or about 125 mM; or about 150 mM; or about 175 mM. In some embodiments, the buffering agent is one or more selected from the group consisting of a citrate buffer, a HEPES buffer, a phosphate buffer, and a Tris buffer. In some embodiments the buffering agent is Tris-HCl. In some embodiments the pH buffering agent is a citrate buffer and is present in an amount between 50-250 mM. In some embodiments the pH buffering agent is a HEPES buffer and is present in an amount between 25-150 mM. In some embodiments the pH buffering agent is a phosphate buffer, and is present in an amount between 50-200 mM. In some embodiments the pH buffering agent is a Tris buffer (for example Tris-HCl), and is present in an amount between 25-250 mM. The pH buffer may mitigate degradation or fragmentation of nucleic acids contained in the urine sample when the sample is subjected to freezing or defrosting. The pH buffer may in certain embodiments prevent nucleic acid base damage, such as de-purination or deamination.

In some embodiments, a solution of the disclosure includes a crowding agent. In some embodiments, a solution of the disclosure includes a crowding agent wherein the crowding agent is one or more selected from the group consisting of ethanol, isopropanol, and polyethylene glycol (PEG). In some embodiments, a solution of the disclosure includes a crowding agent wherein the crowding agent is PEG and wherein the PEG is one or more selected from the group consisting of PEG 4000, PEG6000, and PEG8000. In some embodiments, a solution of the disclosure includes a crowding agent wherein the crowding agent is one or more selected from the group consisting of ethanol, isopropanol, PEG 4000, PEG6000, and PEG8000. In some embodiments, a solution of the disclosure includes a crowding agent wherein the crowding agent is one or more selected from the group consisting of ethanol, isopropanol, PEG (e.g., PEG 4000, PEG6000, and/or PEG8000); and wherein the crowding agent is present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution. In some embodiments, a solution of the present disclosure includes the crowding agent, ethanol, present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution. In some embodiments, a solution of the present disclosure includes the crowding agent, isopropanol, present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution. In some embodiments, a solution of the present disclosure includes the crowding agent, PEG4000, present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution. In some embodiments, a solution of the present disclosure includes the crowding agent, PEG6000, present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution. In some embodiments, a solution of the present disclosure includes the crowding agent, PEG8000, present in an amount between 10-20%; or 10-15%; or 15-20%; or 12-18%; or 13-17%; or about 10%; or about 11%; or about 12%; or about 13%; or about 14%; or about 15%; or about 16%; or about 17%; or about 18%; or about 19%; or about 20% weight/volume of the solution.

In some embodiments, a solution as provided herein includes a salt, or osmotic agent. In some embodiments, the type and amount of a salt, or osmotic agent, is present in a solution of the disclosure is optimized for preservation and/or evaluation of nucleic acid. In some embodiments, the salt, or osmotic agent, is present in the solution in an amount that is 0.5-2.5M; or 1-2M; or 1.25-1.75M; or 1-1.5M; or 1.5-2M; or 1.5-2.5M; or 2-2.5M; or about 0.5M; or about 0.6M; or about 0.7M; or about 0.8M; or about 0.9M; or about 1.0M; or about 1.1M; or about 1.2M; or about 1.3M; or about 1.4M; or about 1.5M; or about 1.6M; or about 1.7M; or about 1.8M; or about 1.9M; or about 2.0M; or about 2.1M or about 2.2M; or about 2.3M; or about 2.4M; or about 2.5M. In some embodiments the salt, or osmotic agent, is sodium chloride (NaCl). In some embodiments the salt, or osmotic agent, is sodium chloride (NaCl) present in an amount that is 0.5-2.5M; or 1-2M; or 1.25-1.75M; or 1-1.5M; or 1.5-2M; or 1.5-2.5M; or 2-2.5M; or about 0.5M; or about 0.6M; or about 0.7M; or about 0.8M; or about 0.9M; or about 1.0M; or about 1.1M; or about 1.2M; or about 1.3M; or about 1.4M; or about 1.5M; or about 1.6M; or about 1.7M; or about 1.8M; or about 1.9M; or about 2.0M; or about 2.1M or about 2.2M; or about 2.3M; or about 2.4M; or about 2.5M.

In some embodiments, a solution as described herein is provided wherein the solution includes a cationic polymer selected from the group consisting of Poly-L-Arginine, Poly-D-Lysine, and Poly-L-Lysine. In some embodiments, the solution of any embodiments herein includes a cationic polymer selected from the group consisting of Poly-L-Arginine, Poly-D-Lysine, and Poly-L-Lysine; wherein the cationic polymer is present in the solution in an amount that is 1-100 µgg/mL; or 1-10 µg/mL; or 10-20 µg/mL; or 20-30 µg/mL; or 30-40 µg/mL; or 40.50 µg/mL; or 50-60 µg/mL; or 60-70 µg/mL; or 70-80 µg/mL; or 80-90 µg/mL; or 90-100 µg/mL; or 1-25 µg/mL; or 10-15 µg/mL; or about 8 µg/mL; or about 10 µg/mL; or about 12.5 µg/mL; or about 15 µg/mL; or about 20 µg/mL; or about 25 µg/mL or about 50 µg/mL; or about 75 µg/mL; or about 100 µg/mL. In some embodiments, a solution as described herein is provide wherein the solution includes Poly-L-Arginine; wherein the Poly-L-Arginine has a molecular weight between 5,000-15,000. In some embodiments, a solution as described herein is provide wherein the solution includes Poly-L-Arginine; wherein the Poly-L-Arginine has a molecular weight between 15,000-75,000. In some embodiments, a solution as described herein is provide wherein the solution includes Poly-L-Arginine; wherein the Poly-L-Arginine has a molecular weight is greater than 70,000. In some embodiments, a solution as described herein is provide wherein the solution includes Poly-D-Arginine; wherein the Poly-L-Arginine has a molecular weight greater than 300,000. In some embodiments, a solution as described herein is provide wherein the solution includes Poly-L-Arginine; wherein the Poly-L-Arginine is present in the solution in an amount that is 1-100 µg/mL; or 1-10 µg/mL; or 10-20 µg/mL; or 20-30 µg/mL; or 30-40 µg/mL; or 40.50 µg/mL; or 50-60 µg/mL; or 60-70 µg/mL; or 70-80 µg/mL; or 80-90 µg/mL; or 90-100 µg/mL; or 1-25 µg/mL; or 10-15 µg/mL; or about 8 µg/mL; or about 10 µg/mL; or about 12.5 µg/mL; or about 15 µg/mL; or about 20 µg/mL; or about 25 µg/mL or about 50 µg/mL; or about 75 µg/mL; or about 100 µg/mL. In some embodiments, a solution as described herein is provided wherein the solution includes Poly-L-Lysine; wherein the Poly-L-Lysine has a molecular weight between 1,000-5,000. In some embodiments, a solution as described herein is provide wherein the solution includes Poly-L-Lysine; wherein the Poly-L-Lysine has a molecular weight between 30,000-70,000. In some embodiments, a solution as described herein is provide wherein the solution includes Poly-L-Lysine; wherein the Poly-L-Lysine has a molecular weight between 70,000-150,000. In some embodiments, a solution as described herein is provide wherein the solution includes Poly-L-Lysine; wherein the Poly-L-Lysine has a molecular weight between 150,000-300,000. In some embodiments, the poly-L-lysine may have a molecular weight of at least about 100 Daltons (Da), 200 Da, 300 Da, 400 Da, 500 Da, 600 Da, 700 Da, 800 Da, 900 Da, 1,000 Da, 2,000 Da, 3,000 Da, 4,000 Da, 5,000 Da, 6,000 Da, 7,000 Da, 8,000 Da, 9,000 Da, or 10,000 Da, or more. The poly-L-lysine may have a molecular weight of at most about 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, or 100 Da, or less. The poly-L-lysine may have molecular weight that is within a range defined by any two of the preceding values, and multiple species of different size ranges may be included together in various ratios. For instance, the poly-L-lysine may have a molecular weight that is within a range from 1,000 Da to 5,000 Da. One preferred embodiment may include poly-L-lysine trimers with a molecular weight of 402.53 Da. A combination of molecular weights may be used together to facilitate both cell membrane stabilization and optimal DNA compaction. For example, various ratios of poly-L-lysine species may be used, such as about 10%, 20%, 30% 40% 50%, or 60% of species being in the range of 1,000-5,000 Da and the other about 90%, 80%, 70%, 60%, 50%, or 40% of species being in the range of around 400 Da. In some embodiments, a solution as described herein is provided wherein the solution includes Poly-L-Lysine; wherein the Poly-L-Lysine is present in the solution in an amount that is 1-100 µg/mL; or 1-10 µg/mL; or 10-20 µg/mL; or 20-30 µg/mL; or 30-40 µg/mL; or 40.50 µg/mL; or 50-60 µg/mL; or 60-70 µg/mL; or 70-80 µg/mL; or 80-90 µg/mL; or 90-100 µg/mL; or 1-25 µg/mL; or 10-15 µg/mL; or about 8 µg/mL; or about 10 µg/mL; or about 12.5 µg/mL; or about 15 µg/mL; or about 20 µg/mL; or about 25 µg/mL or about 50 µg/mL; or about 75 µg/mL; or about 100 µg/mL. In some embodiments Poly-L-Lysine in a solution as provided herein may protect the nucleic acids by compacting free nucleic acids, such as by engaging in transient electrostatic or other charge-based associations with the nucleic acids. In some embodiments, the Poly-L-Lysine many be a Poly-L-Lysine hydrobromide.

In some embodiments of the solutions provided herein the solution includes an antimicrobial. As used herein, an antimicrobial is an agent that kills a microorganism, or stops or slows the growth or division of a microorganism. In some embodiments, an antimicrobial is an antibiotic, antiviral or antimycotic. In some embodiments an antimicrobial is approved by a government regulatory agency or authority (such as the United States Food and Drug Administration, U.S. FDA) as an antimicrobial, for example approved as an antibiotic, antiviral or antimycotic. In some embodiments the antimicrobial is one or more selected from a group consisting of penicillin, streptomycin, Amphotericin B (Fungizone), and a urine Stabilur tablet. In certain embodiments of the solutions provided herein one or more antimicrobials are present in the solution in an amount that is effective to kill a microorganism or stops or slows the growth or division of a microorganism. In certain embodiments of the solutions provided herein one or more antimicrobials are present in the solution in an amount that is effective to kill a microorganism, or stops or slows the growth or division of most or all microorganisms that could be in the solution. In some embodiments, a solution as provided herein includes penicillin in an amount that is 25-250 Units/ml; or 50-200 Units/ml; or 100-150 Units per/ml; 50-75 Units/ml; or 70-80 Units/ml; or 80-90 Units/ml; or 90-100 Units/ml; or 100-110 Units/ml; or 110-120 Units/ml; or 120-130 Units/ml; or 130-140 Units/ml; or 140-150 Units/ml; or 150-175 Units/ml; or about 100 Units/ml; or about 125 Units/ml; or about 150 Units/ml; or about 175 Units/ml. In some embodiments, a solution as provided herein includes streptomycin in an amount that is 25-250 µg/ml; or 50-200 µg/ml; or 100-150 µg per/ml; 50-75 µg/ml; or 70-80 µg/ml; or 80-90 µg/ml; or 90-100 µg/ml; or 100-110 µg/ml; or 110-120 µg/ml; or 120-130 µg/ml; or 130-140 µg/ml; or 140-150 µg/ml; or 150-175 µg/ml; or about 100 µg/ml; or about 125 µg/ml; or about 150 µg/ml; or about 175 µg/ml. In some embodiments, a solution as provided herein includes amphotericin B in an amount that is 100-500 ng/ml; or 200-400 ng/ml; or 100-200 ng/ml; or 200-300 ng/ml; or 250-350 ng/ml; or 300-400 ng/ml; or 350-450 ng/ml; or 400-500 ng/ml; or about 150 ng/ml; or about 175 ng/ml; or about 200 ng/ml; or about 212 ng/ml; or about 225 ng/ml; or about 250 ng/ml; or about 262 ng/ml; or about 275 ng/ml; or about 287 ng/ml; or about 300 ng/ml; or about 312 ng/ml; or about 325 ng/ml; or about 350 ng/ml; or about 375 ng/ml; or about 400 ng/ml; or about 425 ng/ml; or about 450 ng/ml; or about 500 ng/ml. In some embodiments a solution as provided herein includes a mixture of antimicrobial agents. In some embodiments a solution as provided herein includes penicillin, streptomycin and Amphotericin B. In some embodiments a solution as provided herein includes 125 Units/ml penicillin, 125 mg/ml streptomycin, 312 ng/ml Amphotericin B. In some embodiments, the antimicrobial agent may comprise at least 1, 2, or 3 member(s) selected from the group consisting of: penicillin, streptomycin, and amphotericin B. The antimicrobial agent may comprise at most 3, 2, or 1 member(s) selected from the group consisting of: penicillin, streptomycin, and amphotericin B. The antimicrobial agent may comprise a number of member(s) that is within a range defined by any two of the preceding values. In certain embodiments, a solution as provided herein may include one or more; or two or more; or three or more antimicrobials selected from the group consisting of Aminoglycosides, Amikacin, Gentamicin, Kanamycin, Neomycin, Netilmicin, Tobramycin, Paromomycin, Streptomycin, Spectinomycin(Bs), Ansamycins, Geldanamycin, Herbimycin, Rifaximin, Carbacephem, Loracarbef, Carbapenems, Ertapenem, Doripenem, Imipenem/Cilastatin, Meropenem, Cephalosporins, Cefadroxil, Cefazolin, Cephradine, Cephapirin, Cephalothin, Cefalexin, Cephalosporins, Cefaclor, Cefoxitin, Cefotetan, Cefamandole, Cefmetazole, Cefonicid, Loracarbef, Cefprozil, Cefuroxime, Cephalosporins, Cefixime, Cefdinir, Cefditoren, Cefoperazone, Cefotaxime, Cefpodoxime, Ceftazidime, Ceftibuten, Ceftizoxime, Moxalactam, Ceftriaxone, Cephalosporins, Cefepime, Cephalosporins (Fifth generation), Ceftaroline, fosamil, Ceftobiprole, Glycopeptides, Teicoplanin, Vancomycin, Telavancin, Dalbavancin, Oritavancin, Lincosamides(Bs), Clindamycin, Lincomycin, Lipopeptide, Daptomycin, urine Stabilur tablet, Macrolides(Bs), Azithromycin, Clarithromycin, Erythromycin, RoxithromycinTelithromycin, Spiramycin, Fidaxomicin, Monobactams, Aztreonam, Nitrofurans, Furazolidone, Nitrofurantoin(Bs), Oxazolidinones(Bs), Linezolid, Posizolid, Radezolid, Torezolid, Penicillins, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Penicillin combinations, Amoxicillin/clavulanate, Ampicillin/sulbactam, Piperacillin/tazobactam, Ticarcillin/clavulanate, Polypeptides, Bacitracin, Colistin, Polymyxin B, Quinolones/Fluoroquinolones, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin, Sulfonamides (Bs), MafenideSulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Tetracyclines (Bs), Demeclocycline, Doxycycline, Metacycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin (Rifampin in US), Rifabutin, Rifapentine, Streptomycin, Others, Arsphenamine, Chloramphenicol(Bs), Fosfomycin, Fusidic acid, Metronidazole, Mupirocin, Platensimycin, Quinupristin/Dalfopristin, Thiamphenicol, Tigecycline(Bs), Tinidazole, and Trimethoprim(Bs). In certain other embodiments, an antimicrobial of a solution as provided herein may one or more siderophores selected from the group consisting of Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Deferoxamine Mesylate, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, *Dimerum* acid, Dimethylcoprogen, Dimethylneocoprogen, Dimethyltriomicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopropen, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriomicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin 51, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin.

In some embodiments, a solution of the disclosure includes a chelating agent, a detergent, a salt, a cationic polymer, a pH buffering agent, a crowding agent, paramagnetic beads and an antimicrobial; wherein the chelating agent is present in an amount between either 25-750 uM or 10-100 mM in the solution; wherein the detergent is present in an amount between 0.1-1.0% weight/volume of the solution; wherein the salt is present in an amount between 1-2M in the solution; wherein the cationic polymer is present in an amount between 10-100 mg/L in the solution; and wherein the crowding agent is present in an amount between 10-20% of the solution. In some similar embodiments, a solution of the disclosure includes a chelating agent, a detergent, a salt, a cationic polymer, a pH buffering agent, a crowding agent, paramagnetic beads and an antimicrobial; wherein the chelating agent is present in an amount between either 25-750 μM or 10-100 mM in the solution; wherein the detergent is present in an amount between 0.1-1.0% weight/volume of the solution; wherein the salt is present in an amount between 1-2M in the solution; wherein the cationic polymer is present in an amount between 10-100 mg/L in the solution; and wherein the crowding agent is present in an amount between 10-20% of the solution; and wherein the solution further includes paramagnetic beads and an antimicrobial.

In some embodiments a solution of the present disclosure includes paramagnetic beads. As used herein the term "paramagnetic beads" means beads that have an affinity for nucleic acid and can be used to extract nucleic acid from a sample. In some embodiments, the paramagnetic beads are 10 nm-10 μm. In some embodiments, the paramagnetic beads are 100 nm-10 μm; or 500 nm-5 μm; or 500 nm-2 μm; or 500 nm-1.5 μm; or 750 nm-1.25 μm; or about 500 nm; or about 600 nm; or about 700 nm; or about 750 nm; or about 800 nm; or about 900 nm; or about 1 μm; or about 1.1 μm; or about 1.2 μm; or about 1.25 μm; or about 1.3 μm; or about 1.4 μm; or about 1.5 μm. In some embodiments, the paramagnetic beads are 1-100 nm; or 10-50 nm; or 10-20 nm; or 20-30 nm; or 30-40 nm; or 40-50 nm; or 5-25 nm; or 15-35 nm; or 20-40 nm. Bead sizes stated herein are expressed as average diameter size. In certain embodiments, the paramagnetic beads comprise an iron oxide such as magnetite (Fe3O4) which give the beads superparamagnetic properties. In some embodiments, the paramagnetic beads include 30-70% magnetite; or 40-60% magnetite; or 30-50% magnetite; or 35-45% magnetite; or 40-50% magnetite; or 50-70% magnetite; or 55-65% magnetite; or about 30% magnetite; or about 35% magnetite; or about 40% magnetite; or about 45% magnetite; or about 50% magnetite; or about 55% magnetite; or about 60% magnetite; or about 65% magnetite; or about 70% magnetite. Beads with superparamagnetic properties exhibit magnetic activity only in the presence of an external magnetic field, enabling the beads to be used without clumping without an external magnetic field and then be separated from the solution when exposed to an external magnetic field. In certain embodiments, In some embodiments of the compositions and methods provided herein the beads are present in a solution (such as a preservation/extraction solution as described) in an amount that is 1 mg/L-10 g/L; or 5 mg/L-5 g/L; or 25 mg/L-2.5 g/L; or 50 mg/L-1 g/L; or 50 ng/L-500 mg/L; or 50 mg/L-200 mg/L; or 50 mg/L-150 mg/L; or 75 mg/L-125 mg/L; or about 1 mg/L; or about 10 mg/L; or about 50 mg/L; or about 60 mg/L; or about 70 ng/L; or about 75 mg/L; or about 80 mg/L; or about 90 mg/L; or about 100 mg/L; or about 110 mg/L; or about 120 mg/L; or about 125 mg/L; or about 1.30 mg/L; or about 140 mg/L; or about 150 mg/L; or about 75 mg/L; or about 200 mg/L; or about 250 mg/L; or about 500 mg/L; or about 750 mg/L; or about 1.0 μL; or about 2.5 g/L; or about 5 g/L; or about 7.5 g/L; or about 10 g/L. In many embodiments the beads comprise or are coated with a substance having an affinity for nucleic acids, for example carboxylate modified beads that can hybridize with nucleic acid for direct capture, amine-blocked beads, oligo(dT)

beads that hybridize mRNA with poly-A tails, streptavidin beads, silica based or coated bead composition or method of any one of the preceding claims wherein solutions used do not includes that reversibly bind nucleic acids. In some embodiments the paramagnetic beads are carboxylate modified (or carboxylate conjugated). In some embodiments the paramagnetic beads are silica coated. In some embodiments the paramagnetic beads are functional group modified (e.g, carboxy, amine, or other functional groups). In some embodiments the paramagnetic beads are amine-modified. In some embodiments, the paramagnetic beads are ligand-modified. In various embodiments a biological sample as described herein is added to a solution of the disclosure that includes paramagnetic beads, and nucleic acid from the biological sample binds to the beads while in the solution. The solution is then exposed to a magnetic field to attract the beads to a specific location such as the edge of a tube containing the solution, allowing the solution to be washed and the sample nucleic acids to be extracted and isolated from the solution. In many embodiments solutions of the disclosure having the magnetic beads and associated extraction/isolation methods are amenable to high-throughput nucleic acid processing and analysis. Some examples of compositions and methods involving paramagnetic beads that can be useful with the compositions and methods described herein can be found in U.S. Pat. No. 5,705,628; He et al, Nature Scientific Reports 7:45199, DOI:10.1038, srep45199 (2017); and Berensmeier, *Appl Microbiol Biotechnol*, 2006, 73(3):495-504, hereby incorporated by reference in their entirety.

In some embodiments, a solution is provided that includes a chelating agent, a detergent, a salt, a cationic polymer, a pH buffering agent, a crowding agent, paramagnetic beads and an antimicrobial, wherein the chelating agent is one or more selected from the group consisting of enterobactin, deferasirox (DFS), deferiprone (DFP), deferoxamine mesylate, EDTA, and EGTA; wherein the detergent includes one or more selected from the group consisting of cholate, deoxycholate, sodium dodecyl sulfate, sarkosyl, DDM, digitonin, NP-40, Triton X-100, Tween 20, and Tween 80; wherein the salt is sodium chloride; wherein the cationic polymer is one or more selected from the group consisting of Poly-L-Arginine, Poly-D-Lysine, and Poly-L-Lysine; wherein the crowding agent includes one or more selected from the group consisting of Ethanol, Isopropanol, PEG 4000, PEG6000, and PEG8000; and wherein the antimicrobial is one or more selected from a group consisting of penicillin, streptomycin, Amphotericin B, and a urine stabilur tablet.

In some embodiments, a solution of the present disclosure includes a chelating agent, a detergent, a salt, a cationic polymer, a pH buffering agent, a crowding agent, paramagnetic beads and an antimicrobial; wherein the chelating agent is one or more selected from the group consisting of enterobactin, deferasirox (DFS), deferiprone (DFP), deferoxamine mesylate, EDTA, and EGTA, wherein the chelating agent is present in an amount between either 25-750 µM or 10-100 mM in the solution; wherein the detergent comprises one or more selected from the group consisting of Cholate, Deoxycholate, Sodium Dodecyl Sulfate, Sarkosyl, DDM, Digitonin, NP-40, Triton X-100, Tween 20, and Tween 80, and wherein the detergent is present in an amount between 0.1-1.0% of the solution; wherein the salt is sodium chloride, and wherein the salt is present in an amount of 1.5M in solution; wherein the cationic polymer comprises one or more selected from the group consisting of Poly-L-Arginine, Poly-D-Lysine, and Poly-L-Lysine, and wherein the cationic polymer is present in an amount between 10-100 mg/L in the solution; wherein the crowding agent comprises on or more selected from the group consisting of Ethanol, Isopropanol, PEG 4000, PEG6000, and PEG8000, and wherein the crowding agent is present in an amount between 10-20% of the solution; and wherein the antimicrobial is selected from a group consisting of penicillin, streptomycin, Amphotericin B, and a urine stabilur tablet.

In some embodiments, provided is a solution of any of the embodiments provided herein wherein nucleic acid is stable in the solution for at least seven days at room temperature. In some embodiments, provided is a solution of any of the embodiments provided herein wherein nucleic acid is stable in the solution for at least one day, or two days, or three days, or four days, or five days, or six days, or seven days, or two weeks, or three weeks, or four weeks or five weeks, or six weeks, or seven weeks, or three months, or four months, or five months, or six months, or eight months, or twelve months, or two years, or three years, or four years at room temperature. The term "stable" as used herein with regard to nucleic acid means nucleic acid that serves as a viable template for nucleic acid analysis. Wherein types of nucleic acid analysis could include but are not limited to: polymerase chain reaction (PCR) amplification, nucleic acid sequencing, isothermal amplification, and hybridization pull down. Stability of nucleic acid can be determined by any of many ways well known in the art. For example, in some embodiments nucleic acid may be considered stable if (1) the molecule remains intact, as assessed by gel/capillary electrophoresis, (2) the template portion of the molecule remains intact, as assessed by PCR, (3) sequence integrity is intact, as assessed by nucleic acid sequencing, after a specified period of time. In some embodiments, nucleic acid stability may be determined 6 hours, 12 hours, 18 hours, 24 hours, two days, three days, four days, five days, six days, seven days, eight days, nine days, ten days, two weeks, three weeks, one month, two months, three months, four months, five months, six months, one year, two years or more after the nucleic acid is added to a solution, such as a solution as contemplated herein.

In some embodiments of the solutions provided herein, the solution is a collection/preservation, and extraction solution for preserving nucleic acids from a biological sample. In some embodiments, a solution as provided herein is a preservation, and extraction solution for preserving nucleic acids from a biological sample, wherein the nucleic acid is DNA. In some embodiments, a solution as provided herein is a preservation, and extraction solution for preserving nucleic acids from a biological sample, wherein the nucleic acid is RNA. In some embodiments, a solution as provided herein is a preservation, and extraction solution for preserving nucleic acids from a biological sample, wherein the nucleic acids are from a biological sample to that has, is suspected of having, or is at risk to have, nucleic acid from a pathogen. In some embodiments, a solution as provided herein is a preservation, and extraction solution for preserving nucleic acids from a biological sample, wherein the nucleic acids are from a biological sample to that has, is suspected of having, or is at risk to have, nucleic acid from a pathogen; wherein the pathogen is one or more selected from the group consisting of (1) viruses of families including, but not limited to, Adenoviridae, Herpesviridae, Papillomaviridae, Polyomarviridae, Poxviridae, Parvoviridae, Reoviridae, Astroviridae, Caliciviridae, Coronaviridae, Flaviviridae, Hepeviridae, Matonaviridae, Picornaviridae, Arenaviridae, Bunyarviridae, Filoviridae, Orthomyxoviridae, Paramyxoviridae, Pneumoviridae, Rhabdoviridae, Retroviridae, and Hepadnaviridae, (2) bacteria of genera including, but not limited to, *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia*, (3) fungi of genera including, but not limited to, *Aspergillus, Candida, Cryptococcus, Histoplasma, Pneumocystis,* and *Stachybotrys*, and (4) protozoa and algae including, but not limited to, Prototheca wickerhami, *Plasmodium, Entamoeba, Giardia, Trypanosoma brucei, Toxoplasma gondii, Acanthamoeba, Leishmania, Babesia, Balamuthia mandrillaris, Cryptosporidium, Cyclospora,* and *Naegleria fowler*. In some embodiments of the solutions of the disclosure, nucleic acid is stable 6 hours, 12 hours, 18 hours, 24 hours, two days, three days, four days, five days, six days, seven days, eight days, nine days, ten days, two weeks, three weeks, one month, two months, three months, four months, five months, six months, one year, two years or more after the nucleic acid is added to the solution.

As used herein the term "biological sample" is any sample collected from a biological source or that includes, or may include, any matter from a biological source. In some embodiments a biological sample as used herein is any sample that includes, or may include, nucleic acid. In some embodiments, a biological sample is a sample collected from an animal. In some embodiments, a biological sample is a sample collected from a human. In some embodiments a biological sample is a sample collected from a plant. In some embodiments a biological sample may include one or more selected from the group consisting of urine, blood, plasma, serum, mucus, saliva, ophthalmic liquid, feces, cells, and tissue. In certain embodiments, a biological sample is any sample that is suspected of having, or may have, a pathogen. In certain embodiments, a biological sample is any sample that is suspected of having, or may have, nucleic acid of a pathogen. In certain embodiments, a biological sample is any sample that is suspected of having, or may have, nucleic acid. In some embodiments, a biological sample is any sample that is suspected of having, or may have, nucleic acid, wherein there is an interest or desire in detecting or analyzing the nucleic acid. In some embodiments, a nucleic acid of the disclosure is RNA. In some embodiments, a nucleic acid of the disclosure is DNA. In some embodiments, the biological sample is from animal effluent or sewage; for example, in some embodiments the biological sample is from sewage from a building and is useful to determine if an individual that had been in a building may be infected with a pathogen. In certain embodiments a biological sample may be a food product. In some embodiments, a biological sample may be a food product that is suspected of having, or may have, nucleic acid. In some embodiments, a biological sample may be a food product that is suspected of having, or may have, a pathogen. In some embodiments, a biological sample may be a food product that is suspected of having, or may have, nucleic acid from a pathogen. In certain embodiments, a food product as used herein is any product that is intended for human consumption. In certain embodiments, a food product as used herein is may be a beverage, water, produce, fruit, vegetable, grain, cereal, processed food, bread, cracker, cookie, meat, processed meat and the like. In some embodiments, a biological sample may be from livestock and/or poultry. In some embodiments a biological sample is from a commodity such as meat, eggs, milk, fur, leather, or wool. In some embodiments, the biological sample is from effluent and/or animal waste from a farm with domesticated animals such as livestock or poultry. In some embodiments, a biological sample may be taken from a slaughterhouse. In some embodiments, a biological sample may be taken from a carcass from a slaughterhouse. In some embodiments, a biological sample may be from chicken carcass wash. In some embodiments, a biological sample may be taken livestock carcass wash. In some embodiments, a biological sample may be from a carcass of an animal that died or exhibited weakness or illness prior to slaughter. In some embodiments, a biological sample may be a sample from an environmental source that is suspected of having, or may have, nucleic acid. In some embodiments, a biological sample may be a sample from an environmental source that is suspected of having, or may have, a pathogen. In some embodiments, a biological sample may be a sample from an environmental source that is suspected of having, or may have, nucleic acid from a pathogen. In some embodiments, a biological sample from an environmental source is any sample collected from the environment. In some embodiments, a sample from an environmental source is a water sample, a water sample from an ocean, a water sample from a bay or estuary, a water sample from a river, a water sample from a swamp, a water sample from a lake, a water sample from a swimming pool, a soil sample, and the like. In some embodiments as used herein a biological sample is collected by nasal swab. In some embodiments as used herein a biological sample is collected by throat swab. In some embodiments as used herein a biological sample is collected by nasopharyngeal swab. In some embodiments as used herein a biological sample is collected by vaginal swab. In some embodiments as used herein a biological sample is collected by penile meatal swab. In some embodiments as used herein a biological sample is collected by rectal swab. In some embodiments as used herein a biological sample is collected by urogenital swab of vagina, cervix, discharge, aspirated endocervical, endometrial, semen, prostatic fluid, or urethral discharge. In some embodiments a biological sample includes, or may include, nucleic acids. In some embodiments a biological sample used herein includes DNA. In some embodiments a biological sample used herein includes RNA. A biological sample of certain embodiments provided herein may be a biological sample suspected of having nucleic acids from a pathogen. In certain embodiments, a biological sample is collected from a subject suspected to be infected with the SARS-CoV2 virus. In certain embodiments, a biological sample is collected from a subject desiring to be tested for infection with the SARS-CoV2 virus.

In a second aspect a kit is provided, wherein the kit includes a solution of any of the embodiments provided herein. In some embodiments the kit includes one or more receptacles that have a solution as provided herein. In certain embodiments of a kit, the solution as provided herein in a multi-well plate. In some embodiments of a kit, the solution and plate are integrated into a testing system which includes other reagents enabling the detection or measurement of specific nucleic acid sequences. In some embodiments, the kit includes a solution as provided herein in a tube. In certain embodiments, the tube has a solution as contemplated herein and is configured to accept a biological sample into the solution. In certain embodiments, the tube has a solution as contemplated herein and is configured to accept a biological sample from a sampling swab into the solution. In certain embodiments, the kit contains a tube with a solution as described herein and a sampling device suitable for collecting a biological sample from a subject. In some embodiments, the tube is configured to be suitable for high throughput nucleic acid extraction and evaluation. In some embodiments a tube, as used herein, is a well in a plate such as a 48 or 96 well plate. In some embodiments, a kit as provided herein is configured to be suitable for high throughput nucleic acid extraction and evaluation. In various embodiments, the kit is configured to be used in any embodiments of the methods provided herein. In certain embodiments, the kit is used in any embodiments of the methods provided herein.

In various aspects and embodiments of the compositions and methods provided herein, nucleic acid from a sample (such as a biological sample) is detected and/or analyzed. For example, some embodiments involve evaluating nucleic acid for the presence or absence of a genetic marker or for nucleic acid associated with a pathogen, or a variant of a pathogen. In some embodiments, the nucleic acid and/or detection may involve nucleic acid amplification methods, PCR, RT-PCR, quantitative PCR, RFLP analysis, nucleic acid sequencing, next-generation sequencing, nucleic acid hybridization analyses, northern blotting, southern blotting, or the like. In some embodiments, the nucleic acid detection and/or analysis includes nucleic acid amplification. Nucleic acid can be amplified by one of the alternative methods for amplification well known in the art, which include for example: polymerase chain reaction (PCR); multiplex PCR that allows the simultaneous amplification of several DNA sequences; multiplex ligation-dependent probe amplification (MLPA) for the amplification of multiple targets using a single pair of primers; quantitative PCR (qPCR), which measures and quantify the amplification in real time; ligation chain reaction (LCR) that uses primers covering the entire sequence to amplify, thereby preventing the amplification of sequences with a mutation; rolling circle amplification (RCA), wherein the two ends of the sequences are joined by a ligase prior to the amplification of the circular DNA; helicase dependent amplification (HDA) which relies on a helicase for the separation of the double stranded DNA; loop mediated isothermal amplification (LAMP) which employs a DNA polymerase with high strand displacement activity; the nucleic acid sequence based amplification, specifically designed for RNA targets; strand displacement amplification (SDA) which relies on a strand-displacing DNA polymerase, to initiate replication at nicks created by a strand-limited restriction endonuclease or nicking enzyme at a site contained in a primer; the multiple displacement amplification (MDA), based on the use of the highly processive and strand displacing DNA polymerase from the bacteriophage 029; the Xmap® technology of Luminex that allows the simultaneous analysis of up to 500 bioassays through the reading of biological test on the surface of microscopic polystyrene bead. I certain embodiments the analysis and/or detection of nucleic acid may involve gel electrophoresis using agarose or polyacrylamide gel; ethidium bromide staining (a DNA intercalant), labeled probes (radioactive or non-radioactive labels, southern blotting), labeled deoxyribonucleotides (for the direct incorporation of radioactive or non-radioactive labels) or silver staining for the direct visualization of amplified PCR products; restriction endonuclease digestion; high-performance liquid chromatography (HPLC); dot blots; hybridization of amplified DNA on specific labeled probes (radioactive or non-radioactive labels); high-pressure liquid chromatography using ultraviolet detection; electrochemiluminescence coupled with voltage-initiated chemical reaction/photon detection; direct sequencing using radioactive or fluorescently labeled deoxyribonucleotides for the determination of the precise order of nucleotides with a DNA fragment of interest; oligo ligation assay (OLA); PCR; qPCR; DNA sequencing, fluorescence, gel electrophoresis, magnetic beads, allele specific primer extension (ASPE) and/or direct hybridization. Examples of nucleic acid analysis may include sequencing. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, direct detection nanopore based sequencing such as Oxford Nanopore, Single Molecule Real-Time Sequencing such as PacBio, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

As used herein, a kit or tube configured to be suitable for high throughput nucleic acid extraction and evaluation includes features such as: a tube amenable to mechanical capping/de-capping, and/or amendable to high throughput accessioning through use of barcode labels, and/or a tube configured for application of a magnetic field to enable the immobilization of paramagnetic nucleic acid binding beads and subsequent washing or buffer exchange on the beads. In some embodiments "high throughput" may refer to a system or kit that involves robotic handling of the samples and or performance of one or more steps of the methods contemplated herein. In some embodiments "high throughput" may refer to a system or kit that may enable extraction and analysis of 20-200 samples per day, or 200-1,000 samples per day, 500-10,000 samples per day, 5,000-50,000 samples per day, 25,000-100,000 samples per day, 50,000-500,000 samples per day. A non-limiting list of exemplary high-throughput systems that could be used with the compositions and methods provided herein include Tecan Freedom Evo, Hamilton STAR, Qiagen QlAsymphony, Chemagic MSM or the King Fisher Flex Liquid Handling System.

As used herein, washing, or a wash solution, or wash buffer, includes exposing beads (possibly having nucleic acid bound to the beads) to a solution removes proteins, salts, and other contaminants but leaves the nucleic acid bound to the beads. In many embodiments, a wash solution or wash buffer is alcohol based.

In a third aspect, a method is provided that involves providing a solution or kit (including a kit that includes a tube with a solution of the disclosure) of any of the aspects or embodiments of the disclosure and contacting a biological sample that includes nucleic acid with the solution. In some embodiments, the method includes providing a solution or kit of any of the aspects and embodiments of the disclosure, contacting a biologic sample that includes nucleic acid with the solution; and subsequently evaluating the nucleic acid for the presence or absence of a genetic marker or for nucleic acid of a pathogen. In some embodiments of the methods of the disclosure, the method includes providing a solution or kit as described herein; contacting a biological sample that includes nucleic acid with the solution; and evaluating the nucleic acid for the presence or absence of a genetic marker or a pathogen without use of a second extraction solution.

In one embodiment, the method involves providing a tube that includes a solution of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed. In one embodiment, the method involves providing a tube that includes a solution of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed. In some embodiments, the method involves providing a tube that includes a solution of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed, and (4) the nucleic acid that was bound to the beads is analyzed for the presence or absence of pathogenic nucleic acid. In one embodiment, the method involves providing a tube that includes a solution of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid. In one embodiment, the methods provided herein involve providing a tube that includes a solution of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid; wherein steps 2, 3 and 4 are performed without the use of a nucleic acid extraction solution other than the solution of step 1. In certain embodiments of the methods provided herein, aside from than the initial preservation/extraction solution as disclosed herein, no additional extraction solution is used in the methods that includes a detergent. In certain embodiments of the methods provided herein, aside from than the initial preservation/extraction solution as disclosed herein, no additional extraction solution is used in the methods that includes a detergent. In certain embodiments of the methods provided herein, aside from than the initial preservation/extraction solution as disclosed herein, no additional extraction solution is used in the methods that includes a detergent or any of the following: guanidine (such a guanidine salt, for example, guanidine thiocyanate, guanidine isothiocyanate, guanidine HCl, thiocyanic acid with guanidine), thiocyanate, sodium iodide, urea, an alkaline solution, or an enzyme such as, for example, proteinase K, trypsin, dispase, collagenase, cellulase, chitinase, lysozyme, lipase, zymolase, or liticase. In some embodiments the methods provided herein do not involve a lysis/extraction that involves a physical method such as one or more of freezing and grinding, exposure to a temperature change (for example a temperature change of more than 10° C.; or 20° C., or 25° C., or 30° C., or 40° C.; or 50° C.; or 60° C.; or 70° C.; or 80° C.; or 90° C.; or 100° C.; or 125° C.; or more), or exposure to high-intensity sound waves (sonication), or exposure to changes in pressure.

In many current standard nucleic acid collection, extraction and analysis methods and systems do not extract or concentrate the entirety of the sample, rather typically take a small percentage of the total sample for extraction and analysis. In samples with low amounts of nucleic acid or pathogen, these sampling and sequential dilution steps can result in loss of nucleic acid material thus impairing the ability to successfully analyze the nucleic acid and increasing false negative results.

Most of such standard methods involve adding (contacting) a biological sample with a solution, and removing an aliquot of the solution having the biological sample for further nucleic acid evaluation; thus resulting in only a portion (often 10% or less) of the nucleic acid of the original biological sample being subjected to the nucleic acid analysis. This can result in lower sensitivity of the nucleic acid evaluation, and in the case of tests to detect presence of nucleic acid (e.g., nucleic acid of a pathogen) the lower sensitivity can result in false negative results. In certain embodiments of the present disclosure, by combining collection, preservation and/or extraction components (in some embodiments including paramagnetic beads) into a single solution that is contacted with the biological sample, all, or most, of the solution (and all or most of the nucleic acid from the biological solution) can be subjected to the nucleic acid analysis—thereby increasing the sensitivity and accuracy of the test or evaluation. For example, typical automation enabled RNA extraction kits on the market today may process a maximum of 300 microliters of solution per extraction. Due to RNA extraction kit shortage many protocols (CDC) and labs extract only 100 µl of starting transport media, swabs are routinely placed in 2-3 ml of transport solution, resulting in 1/20th-1/30th of an initial sample extracted. For routine silica column extraction kits larger elution volumes are required, so again according to CDC protocols a sample is eluted in 100 µl final volume, of which only 5 µl is placed into a testing reaction (another 20-fold dilution). In total between small volume extraction (1/30th) and large volume elution (1/20th) total dilution can be in aggregate up to 1/600th of a sample volume which is finally analyzed. In certain embodiments of the methods disclosed herein, by extracting the entire sample transport media (all material from the swab) using a collection/preservation/extraction solution as described herein, the first source of dilution can be avoided. In the final elution step of some of the methods of the disclosure, paramagnetic beads can be eluted efficiently in smaller volumes than traditional silica columns (30-50 µl as opposed to 100 µl), further minimizing dilution of the sample and improving testing sensitivity. Accordingly, in one aspect a method is provided wherein the method includes providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the beads are isolated from the solution by one or more of exposure to a magnetic field, centrifugation or filtration, (3) the beads are washed and nucleic acid is subsequently eluted, and (4) the nucleic acid that was bound to the beads is analyzed for the presence or absence of pathogenic nucleic acid; wherein at least 30%; or at least 40%; or at least 50%; or at least 60%; or at least 70%; or at least 75%; or at least 80%; or at least 85%; or at least 90%; or at least 95% of the solution of step (1) that was contacted with the biological sample is used in step (2). In another aspect, a method is provided wherein the method includes providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the beads are isolated from the solution by one or more of exposure to a magnetic field, centrifugation or filtration, (3) the beads are washed and nucleic acid is subsequently eluted, and (4) the nucleic acid that was bound to the beads is analyzed for the presence or absence of pathogenic nucleic acid; wherein at least 30%; or at least 40%; or at least 50%; or at least 60%; or at least 70%; or at least 75%; or at least 80%; or at least 85%; or at least 90%; or at least 95% of the total nucleic of the original biological sample is still present after step (2). In yet another aspect, a method is provided wherein the method includes providing a solution of any one of the preceding embodiments; wherein the solution is contacted with a biological sample and wherein at least 30%; or at least 40%; or at least 50%; or at least 60%; or at least 70%; or at least 75%; or at least 80%; or at least 85%; or at least 90%; or at least 95% of the nucleic acid present in the biological sample is subjected to nucleic acid analysis.

In some embodiments of any of the methods as provided herein, the paramagnetic beads (or any other beads used to bind nucleic acid) are isolated from the solution by centrifugation, filtration or the like. In some embodiments of any of the methods as provided herein, the paramagnetic beads (or any other beads used to bind nucleic acid) are isolated from the solution by centrifugation, filtration or the like and are not exposed to a magnetic field.

In certain embodiments, the methods involve providing a tube that includes a solution beads of the instant disclosure with paramagnetic beads having an affinity for nucleic acid; wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed, and (4) the nucleic acid that was bound to the beads is analyzed for the presence or absence of pathogenic nucleic acid; wherein steps 2, 3 and 4 are performed without the use of a nucleic acid extraction solution other than the solution of step 1 and wherein steps 2, 3 and 4 are performed using a high-throughput nucleic acid processing and analysis system. In some embodiments a biological sample is collected from a subject who has, may have, or desires to be tested for a pathogen (such as SARS-COV2). In some embodiments of the methods, the biological sample is collected and is subsequently contacted with the solution; wherein detergents inactivate the infectious agent rendering it no longer infectious, and where the detergents solubilize lipids and proteins to expose the nucleic acid; wherein nucleic acid is exposed to a cationic polymer promoting structured ordering of charged moieties on the nucleic acid, encouraging nucleic acid condensation; wherein nucleic acid is exposed to a crowding agent and salt such as alcohol or PEG and sodium chloride which promotes immobilization of the nucleic acid on a functionalized charged residue on the paramagnetic beads; wherein a tube is received in a laboratory or processing site, is accessioned, and where a magnetic field is applied to the tube to immobilize the beads to the inner side of the tube; wherein immobilized beads are washed with a solution containing an alcohol; wherein concentrated nucleic acid is eluted from the beads with water or nucleic acid buffer; wherein the eluted nucleic acid is analyzed using a test system. In some embodiments of the methods, the biological sample is collected via nasopharyngeal swab from a subject who has, may have, or desires to be tested for a pathogen (such as SARS-COV2) and is subsequently contacted with the solution; wherein detergents inactivate the infectious agent rendering it no longer infectious, and where the detergents solubilize lipids and proteins to expose the nucleic acid; wherein nucleic acid is exposed to a cationic polymer promoting structured ordering of charged moieties on the nucleic acid, encouraging nucleic acid condensation; wherein nucleic acid is exposed to a crowding agent and salt such as alcohol or PEG and sodium chloride which promotes immobilization of the nucleic acid on a functionalized charged residue on the paramagnetic beads; wherein a tube is received in a laboratory or processing site, is accessioned, and where a magnetic field is applied to the tube to immobilize the beads to the inner side of the tube; wherein immobilized beads are washed with a solution containing an alcohol; wherein concentrated nucleic acid is eluted from the beads with water or nucleic acid buffer; wherein the eluted nucleic acid is analyzed using a test system; and wherein a test result is delivered back to a subject an appropriate treatment is applied to the subject according to the test result.

A method, the method comprising providing a solution or kit of any one of the preceding embodiments; wherein a biological sample is contacted with the solution in a vessel or tube; and wherein the nucleic acid is stored, extracted, immobilized, purified and concentrated in said vessel or tube.

In certain embodiments of any of the solutions or methods provided herein, the solutions used do not include guanidine (such a guanidine salt, for example, guanidine thiocyanate, guanidine isothiocyanate, guanidine HCl, thiocyanic acid with guanidine). In some embodiments, the solutions do not include thiocyanate. In some embodiments of any of the solutions or methods provided herein, the solutions used do not include sodium iodide. In some embodiments of any of the solutions or methods provided herein, the solutions used do not include urea. In some embodiments of any of the solutions or methods provided herein, the solutions used do not include an alkaline solution. In some embodiments of any of the solutions or methods provided herein, the solutions used do not include an enzyme such as, for example, proteinase K, trypsin, dispase, collagenase, cellulase, chitinase, lysozyme, lipase, zymolase, or liticase. In some embodiments of any of the solutions or methods provided herein, the solutions used do not include any of the following: guanidine (such a guanidine salt, for example, guanidine thiocyanate, guanidine isothiocyanate, guanidine HCl, thiocyanic acid with guanidine), thiocyanate, sodium iodide, urea, an alkaline solution, or an enzyme such as, for example, proteinase K, trypsin, dispase, collagenase, cellulase, chitinase, lysozyme, lipase, zymolase, or liticase

BRIEF DESCRIPTION OF THE DRAWINGS

Some novel features various aspect and embodiments of this disclosure are set forth with particularity in the appended embodiments. A better understanding of the features and advantages of the present aspect and embodiments can be obtained by reference to the following detailed description that sets forth illustrative embodiments, in which the principles of the invention are utilized, and the accompanying drawings of which.

SPECIFIC EMBODIMENTS

Figure 1:
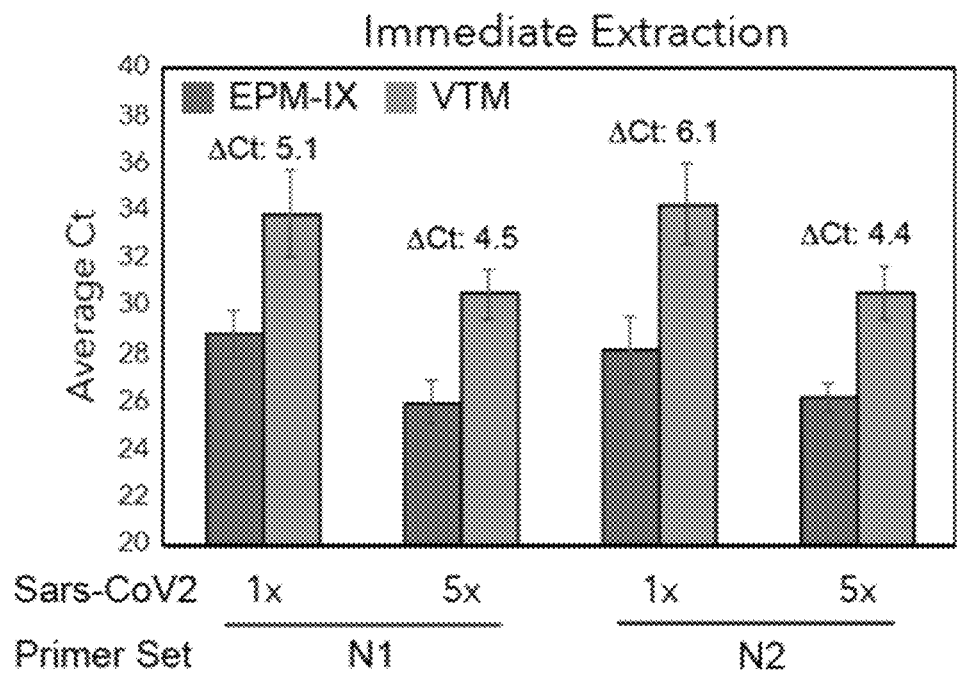
FIG. 1 illustrates an increase in repeatability and stability of the sample in the Enhanced Preservation Media as compared to Viral Transport Media after immediate extraction following exposure to the sample.

In addition to aspects and embodiments contemplated elsewhere in the present disclosure, the following specific embodiments are expressly contemplated:
1. A solution comprising a chelating agent, a detergent, a salt, a cationic polymer and a pH buffering agent.
2. A solution comprising a chelating agent, a detergent, a salt, and a cationic polymer.
3. A solution comprising a chelating agent, a first detergent, a second detergent, a salt, a cationic polymer and a pH buffering agent.
4. A solution comprising a chelating agent, a first detergent, a second detergent, a salt, and a cationic polymer.
5. A solution comprising a first and second chelating agent, a first and second detergent, a salt, a cationic polymer and a pH buffering agent.
6. A solution comprising a chelating agent, a detergent, a salt, a pH buffering agent, a crowding agent and paramagnetic beads.
7. A solution comprising a chelating agent, a detergent, a salt, a crowding agent and paramagnetic beads.
8. A solution comprising a chelating agent, a first detergent, a second detergent, a salt, a pH buffering agent, a crowding agent and paramagnetic beads.
9. A solution comprising a chelating agent, a first detergent, a second detergent, a salt, a crowding agent and paramagnetic beads.
10. A solution comprising a chelating agent, a detergent, a salt, a cationic polymer, a pH buffering agent and an antimicrobial.
11. A solution comprising a chelating agent, a first detergent, a second detergent, a salt, a cationic polymer, a pH buffering agent and an antimicrobial.
12. A solution comprising a chelating agent, a detergent, a salt, a cationic polymer, a pH buffering agent, a crowding agent, paramagnetic beads and an antimicrobial.
13. A solution comprising a chelating agent, a detergent, a salt, a cationic polymer, a crowding agent, paramagnetic beads and an antimicrobial.
14. A solution comprising a chelating agent, a first detergent, a second detergent, a salt, a cationic polymer, a pH buffering agent, a crowding agent, paramagnetic beads and an antimicrobial.
15. solution comprising a chelating agent, a first detergent, a second detergent, a salt, a cationic polymer, a crowding agent, paramagnetic beads and an antimicrobial.
16. A solution comprising a chelating agent, an ionic detergent, a non-ionic detergent, a salt, a cationic polymer, a pH buffering agent, and a crowding agent.
17. A solution comprising a chelating agent, an ionic detergent, a non-ionic detergent, a salt, a cationic polymer, and a crowding agent.
18. A solution comprising a chelating agent, an ionic detergent, a non-ionic detergent, a salt, and a crowding agent and paramagnetic beads.
19. A solution comprising a chelating agent, an ionic detergent that is between 0.1-1.0%, a non-ionic detergent that is between 0.1-1.0%, a salt, a cationic polymer, a pH buffering agent, and a crowding agent.
20. A solution comprising a chelating agent, an ionic detergent that is between 0.1-1.0%, a non-ionic detergent that is between 0.1-1.0%, a salt, a cationic polymer, a pH buffering agent, a crowding agent and paramagnetic beads.
21. A solution comprising a chelating agent, an ionic detergent, a non-ionic detergent, a salt, a cationic polymer, a pH buffering agent, and a crowding agent; wherein the crowding agent is one or more selected from the group consisting of ethanol, isopropanol and PEG.
22. A solution comprising a chelating agent, an ionic detergent, a non-ionic detergent, a salt, a cationic polymer, a pH buffering agent, a crowding agent and paramagnetic beads; wherein the crowding agent is one or more selected from the group consisting of ethanol, isopropanol and PEG.
23. A solution comprising a chelating agent, an ionic detergent that is between 0.1-1.0%, a non-ionic detergent that is between 0.1-1.0%, a salt, a cationic polymer, a pH buffering agent, and a crowding agent; wherein the crowding agent is one or more selected from the group consisting of ethanol, isopropanol and PEG.
24. A solution comprising a chelating agent, an ionic detergent that is between 0.1-1.0%, a non-ionic detergent that is between 0.1-1.0%, a salt, a cationic polymer, a pH buffering agent, a crowding agent and an antimicrobial.
25. A solution comprising a chelating agent, an ionic detergent that is between 0.1-1.0%, a non-ionic detergent that is between 0.1-1.0%, a salt, a cationic polymer, a pH buffering agent, a crowding agent; and an antimicrobial; wherein the crowding agent is one or more selected from the group consisting of ethanol, isopropanol and PEG.
26. A solution comprising a chelating agent, an ionic detergent, a non-ionic detergent, a salt, a cationic polymer, a pH buffering agent, a crowding agent, paramagnetic beads and an antimicrobial agent.

27. A solution comprising a chelating agent, an ionic detergent that is between 0.1-1.0%, a non-ionic detergent that is between 0.1-1.0%, a salt, a cationic polymer, a pH buffering agent, a crowding agent and an antimicrobial agent.

28. A solution comprising a chelating agent, an ionic detergent that is between 0.1-1.0%, a non-ionic detergent that is between 0.1-1.0%, a salt, a cationic polymer, a pH buffering agent, a crowding agent, paramagnetic beads and an antimicrobial; wherein the crowding agent is one or more selected from the group consisting of ethanol, isopropanol and PEG.

29. The solution of any one of the preceding embodiments wherein the solution comprises a chelating agent selected from the group consisting of enterobactin, Deferasirox (DFS), Deferiprone (DFP), Deferoxamine Mesylate (DFM), EDTA, and EGTA.

30. The solution of any one of the preceding embodiments wherein the solution includes a first chelating agent and a second chelating agent.

31. The solution of any one of the preceding embodiments wherein the solution includes a first detergent and a second detergent.

32. The solution of any one of the preceding embodiments, wherein the solution includes an ionic detergent and a non-ionic detergent.

33. The solution of any one of the preceding embodiments wherein the chelating agent is enterobactin.

34. The solution of any one of the preceding embodiments wherein the chelating agent is deferasirox.

35. The solution of any one of the preceding embodiments wherein the chelating agent is deferiprone.

36. The solution of any one of the preceding embodiments wherein the chelating agent is deferoxamine mesylate.

37. The solution of any one of the preceding embodiments wherein the chelating agent is EDTA.

38. The solution of any one of the preceding embodiments wherein the chelating agent is EGTA.

39. The solution of any one of the preceding embodiments wherein the solution comprises a chelating agent that is between 25-750 µM in the solution.

40. The solution of any one of the preceding embodiments wherein the solution comprises a chelating agent that is between 100-200 µM in the solution.

41. The solution of any one of the preceding embodiments wherein the solution comprises a chelating agent that is between 100-150 µM in the solution.

42. The solution of any one of the preceding embodiments wherein the solution comprises a chelating agent that is about 100 µM in the solution.

43. The solution of any one of the preceding embodiments wherein the solution comprises a chelating agent that is about 110 µM in the solution.

44. The solution of any one of the preceding embodiments wherein the solution comprises a chelating agent that is about 120 µM in the solution.

45. The solution of any one of the preceding embodiments wherein the solution comprises a chelating agent that is about 125 µM in the solution.

46. The solution of any one of the preceding embodiments wherein the solution comprises a chelating agent that is about 130 µM in the solution 47. The solution of any one of the preceding embodiments wherein the solution comprises a chelating agent that is about 140 µM in the solution.

48. The solution of any one of the preceding embodiments wherein the solution comprises a chelating agent that is between 10-100 mM in the solution.

49. The solution of any one of the preceding embodiments wherein the solution comprises a chelating agent that is between 50-100 mM in the solution.

50. The solution of any one of the preceding embodiments wherein the solution comprises a chelating agent that is between 50-75 mM in the solution.

51. The solution of any one of the preceding embodiments wherein the solution comprises a chelating agent that is about 50 mM in the solution.

52. The solution of any one of the preceding embodiments wherein the solution comprises a chelating agent that is about 52.5 mM in the solution.

53. The solution of any one of the preceding embodiments wherein the solution comprises a chelating agent that is about 55 mM in the solution.

54. The solution of any one of the preceding embodiments wherein the solution comprises a chelating agent that is about 57.5 mM in the solution.

55. The solution of any one of the preceding embodiments wherein the solution comprises a chelating agent that is about 60 mM in the solution.

56. The solution of any one of the preceding embodiments wherein the solution comprises a chelating agent that is about 62.5 mM in the solution.

57. The solution of any one of the preceding embodiments wherein the solution comprises a chelating agent that is about 65 mM in the solution.

58. The solution of any one of the preceding embodiments wherein the solution comprises a chelating agent that is about 67.5 mM in the solution.

59. The solution of any one of the preceding embodiments wherein the solution comprises a chelating agent that is about 70 mM in the solution.

60. The solution of any one of the preceding embodiments wherein the solution comprises a first chelating agent that is between 50-100 mM in the solution and a second chelating agent that is between 100-150 µM.

61. The solution of any one of the preceding embodiments, wherein the solution comprises a detergent selected from the group consisting of Cholate, Deoxycholate, Sodium Dodecyl Sulfate, Sarkosyl, DDM, Digitonin, NP-40, Triton X-100, Tween 20, and Tween 80.

62. The solution of any one of the preceding embodiments, wherein the solution comprises the detergent Triton X-100.

63. The solution of any one of the preceding embodiments, wherein the solution comprises the detergent Triton X-100 present in an amount between 0.1-1.0% weight/volume of the solution.

64. The solution of any one of the preceding embodiments, wherein the solution comprises detergent cholate.

65. The solution of any one of the preceding embodiments, wherein the solution comprises the detergent cholate in an amount between 0.1-0.5% weight/volume of the solution.

66. The solution of any one of the preceding embodiments, wherein the solution comprises the detergent Deoxycholate. 67. The solution of any one of the preceding embodiments, wherein the solution comprises the detergent Deoxycholate in an amount between 0.1-0.5% weight/volume of the solution.

68. The solution of any one of the preceding embodiments, wherein the solution comprises the detergent Sodium Dodecyl Sulfate.
69. The solution of any one of the preceding embodiments, wherein the solution comprises the detergent Sodium Dodecyl Sulfate in an amount between 0.1-1.0% weight/volume of the solution.
70. The solution of any one of the preceding embodiments, wherein the solution comprises the detergent Sarkosyl.
71. The solution of any one of the preceding embodiments, wherein the solution comprises the detergent Sarkosyl in an amount between 0.5-0.5% weight/volume of the solution.
72. The solution of any one of the preceding embodiments, wherein the solution comprises the detergent DDM.
73. The solution of any one of the preceding embodiments, wherein the solution comprises the detergent DDM in an amount between 0.2-1.0% weight/volume of the solution.
74. The solution of any one of the preceding embodiments, wherein the solution comprises the detergent digitonin.
75. The solution of any one of the preceding embodiments, wherein the solution comprises the detergent digitonin in an amount between 0.2-2.0% weight/volume of the solution.
76. The solution of any one of the preceding embodiments, wherein the solution comprises the detergent NP-40.
77. The solution of any one of the preceding embodiments, wherein the solution comprises the detergent NP-40 in an amount between 0.05-1.0% weight/volume of the solution.
78. The solution of any one of the preceding embodiments, wherein the solution comprises the detergent Tween 20.
79. The solution of any one of the preceding embodiments, wherein the solution comprises the detergent Tween 20 in an amount between 0.05-0.5% weight/volume of the solution.
80. The solution of any one of the preceding embodiments, wherein the solution comprises the detergent Tween 80.
81. The solution of any one of the preceding embodiments, wherein the solution comprises detergent Tween 80 in an amount between 0.05-0.5% weight/volume of the solution.
82. The solution of any one of the preceding embodiments, wherein the solution comprises a buffering agent selected from the group consisting of Citrate, HEPES, Phosphate, and Tris.
83. The solution of any one of the preceding embodiments, wherein the buffering agent is Citrate.
84. The solution of any one of the preceding embodiments, wherein the buffering agent is Citrate, and the buffering agent is present in an amount between 50-250 mM.
85. The solution of any one of the preceding embodiments, wherein the buffering agent is HEPES.
86. The solution of any one of the preceding embodiments, wherein the buffering agent is HEPES, and the buffering agent is present in an amount between 25-150 mM.
87. The solution of any one of the preceding embodiments, wherein the buffering agent is Phosphate.
88. The solution of any one of the preceding embodiments, wherein the buffering agent is Phosphate, and the buffering agent is present in an amount between 50-200 mM.
89. The solution of any one of the preceding embodiments, wherein the buffering agent is Tris.
90. The solution of any one of the preceding embodiments, wherein the buffering agent is Tris, and the buffering agent is present in an amount between 25-250 mM.
91. The solution of any one of the preceding embodiments, wherein the solution comprises a crowding agent selected from the group consisting of Ethanol, Isopropanol, PEG 4000, PEG6000, and PEG8000.
92. The solution of any one of the preceding embodiments, wherein the solution comprises a binding agent selected from the group consisting of Ethanol, Isopropanol, PEG 4000, PEG6000, and PEG8000 and is present in an amount between 10-20% weight/volume of the solution.
93. The solution of any one of the preceding embodiments, wherein the solution comprises binding agent PEG8000 and is present in an amount between 12-18% weight/volume of the solution.
94. The solution of any one of the preceding embodiments, wherein the solution comprises sodium chloride, and is present in an amount between 1-2M in the solution.
95. The solution of any one of the preceding embodiments, wherein the solution comprises a cationic polymer selected from the group consisting of Poly-L-Arginine, Poly-D-Lysine, and Poly-L-Lysine.
96. The solution of any one of the preceding embodiments, wherein the solution comprises a cationic polymer selected from the group consisting of Poly-L-Arginine, Poly-D-Lysine, and Poly-L-Lysine and is present in the solution in an amount between 10-100 mg/L.
97. The solution of any one of the preceding embodiments, wherein the solution comprises an antimicrobial selected from a group consisting of penicillin, streptomycin, Amphotericin B, and a urine Stabilur tablet.
98. The solution of any one of the preceding embodiments, wherein the solution comprises paramagnetic beads.
99. The solution of any one of the preceding embodiments, wherein the solution comprises paramagnetic beads that are 100 nm-10 µm; or 500 nm-5 µm; or 500 nm-2 µm; or 500 nm-1.5 µm; or 750 nm-1.25 µm; or about 500 nm; or about 600 nm; or about 700 nm; or about 750 nm; or about 800 nm; or about 900 nm; or about 1 µm; or about 1.1 µm; or about 1.2 µm; or about 1.25 µm; or about 1.3 µm; or about 1.4 µm; or about 1.5 µm. In some embodiments, the paramagnetic beads are 1-100 nm; or 10-50 nm; or 10-20 nm; or 20-30 nm; or 30-40 nm; or 40-50 nm; or 5-25 nm; or 15-35 nm; or 20-40 nm in diameter.
100. The solution of any one of the preceding embodiments, wherein the solution comprises paramagnetic beads that include 30-70% magnetite; or 40-60% magnetite; or 30-50% magnetite; or 35-45% magnetite; or 40-50% magnetite; or 50-70% magnetite; or 55-65% magnetite; or about 30% magnetite; or about 35% magnetite; or about 40% magnetite; or about 45% magnetite; or about 50% magnetite; or about 55% magnetite; or about 60% magnetite; or about 65% magnetite; or about 70% magnetite.

101. The solution of any one of the preceding embodiments, wherein the solution comprises paramagnetic beads present in the solution in an amount that is 1 mg/L-10 g/L; or 5 mg/L-5 g/L; or 25 mg/L-2.5 g/L; or 50 mg/L-1 g/L; or 50 mg/L-500 mg/L; or 50 mg/L-200 mg/L; or 50 mg/L-150 mg/L; or 75 mg/L-125 mg/L; or about 1 mg/L; or about 10 mg/L; or about 50 mg/L; or about 60 mg/L; or about 70 mg/L; or about 75 mg/L; or about 80 mg/L; or about 90 m about 100 mg/L; about 110 mg/L; or about 120 mg/L; or about 125 mg/L; or about 130 mg/L; or about 140 mg/L; or about 150 mg/L; or about 175 mg/L; or about 200 mg/L; or about 250 mg/L; or about 500 mg/L; or about 750 mg/L; or about 1.0 g/L or about 2.5 g/L; or about 5 g/L; or about 7.5 g/L; or about 10 g/L.

102. The solution of any one of the preceding embodiments, wherein the solution comprises paramagnetic beads; wherein the paramagnetic beads comprise one or more selected from the group consisting of carboxylate modified beads, amine-blocked beads, oligo(dT) beads; streptavidin beads, silica based or coated beads.

103. A solution of any one of the preceding embodiments wherein the solution comprises about 62.5 mM EDTA, 125 μM DFM, 0.5% SDS, 0.5% Triton X, 1.5M NaCl, 12.5 μM Poly-L-Lysine, 125 mM Tris pH8 and 15% PEG8000.

104. A solution of any one of the preceding embodiments wherein the solution comprises about 62.5 mM EDTA, 125 μM DFM, 0.5% SDS, 0.5% Triton X, 1.5M NaCl, 12.5 μM Poly-L-Lysine, 125 mM Tris pH8, 15% PEG8000 and at least one microbial agent.

105. A solution of any one of the preceding embodiments wherein the solution comprises about 62.5 mM EDTA, 125 μM DFM, 0.5% SDS, 0.5% Triton X, 1.5M NaCl, 12.5 μM Poly-L-Lysine, 125 mM Tris pH8, 15% PEG8000, at least one microbial agent and paramagnetic beads.

106. A solution of any one of the preceding embodiments wherein the solution comprises about 62.5 mM EDTA, 125 μM DFM, 0.5% SDS, 0.5% Triton X, 1.5M NaCl, 12.5 μM Poly-L-Lysine, 125 mM Tris pH8, 15% PEG8000, 125 Units/ml penicillin, 125 mg/ml streptomycin, and 312 ng/ml Amphotericin B.

107. A solution of any one of the preceding embodiments wherein the solution comprises about 62.5 mM EDTA, 125 μM DFM, 0.5% SDS, 0.5% Triton X, 1.5M NaCl, 12.5 μM Poly-L-Lysine, 125 mM Tris pH8, 15% PEG8000, 125 Units/ml penicillin, 125 mg/ml streptomycin, 312 ng/ml Amphotericin B and paramagnetic beads.

108. A solution comprising a chelating agent, a detergent, a salt, a cationic polymer, a pH buffering agent, a crowding agent, paramagnetic beads and an antimicrobial, wherein the chelating agent is present in an amount between either 25-750 μM or 10-100 mM in the solution, and wherein the detergent is present in an amount between 0.1-1.0% weight/volume of the solution, and wherein the salt is present in an amount between 1-2M in the solution, and wherein the cationic polymer is present in an amount between 10-100 mg/L in the solution, wherein the buffering agent is present in an amount between 25-250 mM in the solution, and wherein the crowding agent is present in an amount between 10-20% of the solution.

109. A solution comprising a chelating agent, a detergent, a salt, a cationic polymer, a pH buffering agent, a crowding agent, paramagnetic beads and an antimicrobial, wherein the chelating agent comprises one or more selected from the group consisting of enterobactin, deferasirox (DFS), Deferiprone (DFP), Deferoxamine Mesylate, EDTA, and EGTA, wherein the detergent comprises one or more selected from the group consisting of Cholate, Deoxycholate, Sodium Dodecyl Sulfate, sarkosyl, DDM, Digitonin, NP-40, Triton X-100, Tween 20, and Tween 80, wherein the salt is sodium chloride, wherein the cationic polymer comprises one or more selected from the group consisting of Poly-L-Arginine, Poly-D-Lysine, and Poly-L-Lysine, wherein the buffering agent comprises one or more selected from the group consisting of Citrate, HEPES, Phosphate, and Tris, wherein the crowding agent comprises on or more selected from the group consisting of Ethanol, Isopropanol, PEG 4000, PEG6000, and PEG8000, and wherein the antimicrobial is selected from a group consisting of penicillin, streptomycin, Amphotericin B, and a urine stabilur tablet.

110. A solution comprising a chelating agent, a detergent, a salt, a cationic polymer, a pH buffering agent, a crowding agent, paramagnetic beads and an antimicrobial, wherein the chelating agent comprises one or more selected from the group consisting of enterobactin, Deferasirox (DFS), Deferiprone (DFP), Deferoxamine Mesylate, EDTA, and EGTA, wherein the chelating agent is present in an amount between either 25-750 μM or 10-100 mM in the solution; and wherein the detergent comprises one or more selected from the group consisting of Cholate, Deoxycholate, Sodium Dodecyl Sulfate, Sarkosyl, DDM, Digitonin, NP-40, Triton X-100, Tween 20, and Tween 80, and wherein the detergent is present in an amount between 0.1-1.0% of the solution; and wherein the salt is sodium chloride, and wherein the salt is present in an amount of 1.5M in solution; and wherein the cationic polymer comprises one or more selected from the group consisting of Poly-L-Arginine, Poly-D-Lysine, and Poly-L-Lysine, and wherein the cationic polymer is present in an amount between 10-100 mg/L in the solution; wherein the buffering agent comprises one or more selected from the group consisting of Citrate, HEPES, Phosphate, and Tris, and wherein the buffering agent is present in an amount between 25-250 mM in the solution; wherein the crowding agent comprises on or more selected from the group consisting of Ethanol, Isopropanol, PEG 4000, PEG6000, and PEG8000, and wherein the crowding agent is present in an amount between 10-20% of the solution; and wherein the antimicrobial is selected from a group consisting of penicillin, streptomycin, Amphotericin B, and urine Stabilur tablet.

111. A solution comprising a chelating agent, a detergent, a salt, a cationic polymer, a pH buffering agent, a crowding agent, silica-coated beads and an antimicrobial, wherein the chelating agent comprises EDTA, wherein the chelating agent is present in an amount between 10-100 mM in the solution; and wherein the detergents comprise Sodium Dodecyl Sulfate and Triton X-100, and wherein the detergents are both present in an amount of 0.5% of the solution; and wherein the salt is sodium chloride, and wherein the salt is present in an amount of 1.5M in solution; and wherein the cationic polymer comprises Poly-L-Lysine, and wherein the cationic polymer is present in an amount between 10-100 mg/L in the solution; wherein the buffering agent is TRIS, pH 8, and wherein the buffering agent is present at 125 mM in the solution; wherein the crowding agent comprises PEG8000, and wherein the crowding agent is present in an amount between 15% of the solution; and wherein the antimicrobial is selected from a group consisting of penicillin, streptomycin, Amphotericin B, and urine Stabilur tablet.

112. The solution of any of the preceding embodiments wherein the solution is a collection/preservation, and extraction solution.

113. The solution of any of the preceding embodiments wherein the solution is a collection/preservation, and extraction solution for samples from a biological sample containing nucleic acids.

114. The solution of any of the preceding embodiments wherein the solution is a collection/preservation, and extraction solution for samples from a biological sample containing nucleic acids, wherein the nucleic acids bind to paramagnetic beads within the solution.

115. The solution of any one of the preceding embodiments wherein nucleic acid is stable in the solution for at least 6 hours, 12 hours, 18 hours, 24 hours, two days, three days, four days, five days, six days, seven days, eight days, nine days, ten days, two weeks, three weeks, one month, two months, three months, four months, five months, six months, one year, or two years.

116. The solution of any one of the preceding embodiments wherein nucleic acid is stable in the solution for at least 6 hours.

117. The solution of any one of the preceding embodiments wherein nucleic acid is stable in the solution for at least 12 hours.

118. The solution of any one of the preceding embodiments wherein nucleic acid is stable in the solution for at least 18 hours.

119. The solution of any one of the preceding embodiments wherein nucleic acid is stable in the solution for at least 24 hours.

120. The solution of any one of the preceding embodiments wherein nucleic acid is stable in the solution for at least two days.

121. The solution of any one of the preceding embodiments wherein nucleic acid is stable in the solution for at least three days.

122. The solution of any one of the preceding embodiments wherein nucleic acid is stable in the solution for at least four days.

123. The solution of any one of the preceding embodiments wherein nucleic acid is stable in the solution for at least five days.

124. The solution of any one of the preceding embodiments wherein nucleic acid is stable in the solution for at least six days.

125. The solution of any one of the preceding embodiments wherein nucleic acid is stable in the solution for at least seven days.

126. The solution of any one of the preceding embodiments wherein nucleic acid is stable in the solution for at least eight days.

127. The solution of any one of the preceding embodiments wherein nucleic acid is stable in the solution for at least nine days.

128. The solution of any one of the preceding embodiments wherein nucleic acid is stable in the solution for at least ten days.

129. The solution of any one of the preceding embodiments wherein nucleic acid is stable in the solution for at least two weeks.

130. The solution of any one of the preceding embodiments wherein nucleic acid is stable in the solution for at least three weeks.

131. The solution of any one of the preceding embodiments wherein nucleic acid is stable in the solution for at least one month.

132. The solution of any one of the preceding embodiments wherein nucleic acid is stable in the solution for at least two months.

133. The solution of any one of the preceding embodiments wherein nucleic acid is stable in the solution for at least three months.

134. The solution of any one of the preceding embodiments wherein nucleic acid is stable in the solution for at least four months.

135. The solution of any one of the preceding embodiments wherein nucleic acid is stable in the solution for at least five months.

136. The solution of any one of the preceding embodiments wherein nucleic acid is stable in the solution for at least six months.

137. The solution of any one of the preceding embodiments wherein nucleic acid is stable in the solution for at least one year.

138. The solution of any one of the preceding embodiments wherein nucleic acid is stable in the solution for at least two years.

139. A kit comprising a solution of any one of the preceding embodiments.

140. A kit comprising a solution of any one of the preceding embodiments in a tube.

141. A kit comprising a solution of any one of the preceding embodiments; wherein the solution is in a tube configured to accept a biological sample from a sampling swab into the solution.

142. A kit comprising a solution of any one of the preceding embodiments; wherein the solution is in a tube configured to accept saliva into the solution.

143. A kit comprising a solution of any one of the preceding embodiments in a tube and a sample device suitable for collecting a biological sample.

144. A kit comprising a solution of any one of the preceding embodiments in a tube configured to be suitable for high throughput nucleic acid extraction and evaluation.

145. A kit comprising a solution comprising a chelating agent, a detergent, a salt, a cationic polymer and a pH buffering agent in a tube configured to be suitable for high throughput nucleic acid extraction and evaluation.

146. A kit comprising a solution comprising a first and second chelating agent, a first and second detergent, a salt, a cationic polymer and a pH buffering agent in a tube configured to be suitable for high throughput nucleic acid extraction and evaluation.

147. A kit comprising a chelating agent, a detergent, a salt, a pH buffering agent, a crowding agent and paramagnetic beads in a tube configured to be suitable for high throughput nucleic acid extraction and evaluation.

148. A kit comprising a solution comprising a chelating agent, a detergent, a salt, a cationic polymer, a pH buffering agent and an antimicrobial in a tube configured to be suitable for high throughput nucleic acid extraction and evaluation.

149. A kit comprising a solution comprising a chelating agent, a detergent, a salt, a cationic polymer, a pH buffering agent, a crowding agent, paramagnetic beads and an antimicrobial in a tube configured to be suitable for high throughput nucleic acid extraction and evaluation.

150. A kit comprising a solution comprising a chelating agent, a detergent, a salt, a cationic polymer, a pH buffering agent, a crowding agent, paramagnetic beads and an antimicrobial, wherein the chelating agent is present in an amount between either 25-750 µM or 10-100 mM in the solution, and wherein the detergent is present in an amount between 0.1-1.0% weight/volume of the solution, and wherein the salt is present in an amount between 1-2M in the solution, and wherein the cationic polymer is present in an amount between 10-100 mg/L in the solution, and wherein the pH buffering agent is present in an amount between 25-250 mM and wherein the crowding agent is present in an amount between 10-20% of the solution; wherein the solution is in a tube configured to be suitable for high throughput nucleic acid extraction and evaluation.

151. A kit comprising a solution comprising a chelating agent, a detergent, a salt, a cationic polymer, a pH buffering agent, a crowding agent, paramagnetic beads and an antimicrobial, wherein the chelating agent comprises one or more selected from the group consisting of enterobactin, Deferasirox (DFS), Deferiprone (DFP), Deferoxamine Mesylate, EDTA, and EGTA, herein the detergent comprises one or more selected from the group consisting of Cholate, Deoxycholate, Sodium Dodecyl Sulfate, Sarkosyl, DDM, Digitonin, NP-40, Triton X-100, Tween 20, and Tween 80, wherein the salt is sodium chloride, wherein the cationic polymer comprises one or more selected from the group consisting of Poly-L-Arginine, Poly-D-Lysine, and Poly-L-Lysine, wherein the buffering agent comprises one or more selected from the group consisting of Citrate, HEPES, Phosphate, and Tris, wherein the crowding agent comprises on or more selected from the group consisting of Ethanol, Isopropanol, PEG 4000, PEG6000, and PEG8000, and wherein the antimicrobial is selected from a group consisting of penicillin, streptomycin, Amphotericin B, and urine Stabilur tablet; wherein the solution is in a tube configured to be suitable for high throughput nucleic acid extraction and evaluation.

152. A kit comprising a solution comprising a chelating agent, a detergent, a salt, a cationic polymer, a pH buffering agent, a crowding agent, paramagnetic beads and an antimicrobial, wherein the chelating agent comprises one or more selected from the group consisting of enterobactin, Deferasirox (DFS), Deferiprone (DFP), Deferoxamine Mesylate, EDTA, and EGTA, wherein the chelating agent is present in an amount between either 25-750 µM or 10-100 mM in the solution; and wherein the detergent comprises one or more selected from the group consisting of Cholate, Deoxycholate, Sodium Dodecyl Sulfate, Sarkosyl, DDM, Digitonin, NP-40, Triton X-100, Tween 20, and Tween 80, and wherein the detergent is present in an amount between 0.1-1.0% of the solution; and wherein the salt is sodium chloride, and wherein the salt is present in the amount of 1.5M in solution; and wherein the cationic polymer comprises one or more selected from the group consisting of Poly-L-Arginine, Poly-D-Lysine, and Poly-L-Lysine, and wherein the cationic polymer is present in an amount between 10-100 mg/L in the solution; wherein the buffering agent comprises one or more selected from the group consisting of Citrate, HEPES, Phosphate, and Tris, and wherein the buffering agent is present in an amount between 25-250 mM in the solution; wherein the crowding agent comprises on or more selected from the group consisting of Ethanol, Isopropanol, PEG 4000, PEG6000, and PEG8000, and wherein the crowding agent is present in an amount between 10-20% of the solution; and wherein the antimicrobial are selected from a group consisting of penicillin, streptomycin, Amphotericin B, and urine Stabilur tablet; wherein the solution is in a tube configured to be suitable for high throughput nucleic acid extraction and evaluation.

153. A kit, the kit comprising a solution of any one of the preceding embodiments; wherein the solution is in a tube configured to accept a biological sample from a sampling swab into the solution, wherein the swab is contacted with a subject suspected of being infected with a pathogen.

154. A kit, the kit comprising a solution of any one of the preceding embodiments; wherein the solution is in a tube configured to accept a biological sample from a sampling swab into the solution, wherein the swab is contacted with a subject suspected of being infected with a pathogen, wherein the pathogen is SARS-CoV2.

155. A method, the method comprising providing a solution or kit of any one of the preceding embodiments; wherein a biological sample is contacted with the solution.

156. A method, the method comprising providing a solution or kit of any one of the preceding embodiments; wherein a biological sample is contacted with the solution in a vessel or tube; and wherein the nucleic acid is stored, extracted, immobilized, purified and concentrated in said vessel or tube.

157. A method comprising providing a solution or kit of any one of the preceding embodiments; wherein a sample comprising nucleic acid is contacted with the solution; and wherein the nucleic acid from the sample is tested for the presence or absence of a genetic marker or nucleic acid markers of a pathogen.

158. A method comprising providing a solution of any one of the preceding embodiments; wherein a sample comprising nucleic acid is contacted with the solution; and wherein the nucleic acid from the sample is evaluated for the presence or absence of a genetic marker or a pathogen without use of an independent nucleic acid extraction system.

159. A method comprising providing a solution of any one of the preceding embodiments; wherein a sample comprising nucleic acid is contacted with the solution; and wherein the nucleic acid from the sample is evaluated for the presence or absence of a genetic marker or a pathogen without use of an independent nucleic acid extraction system, the pathogen is one or more selected from the group consisting of (1) viruses of families including, but not limited to, Adenoviridae, Herpesviridae, Papillomaviridae, Polyomarviridae, Poxviridae, Parvoviridae, Reoviridae, Astroviridae, Caliciviridae, Coronaviridae, Flaviviridae, Hepeviridae, Matonaviridae, Picornaviridae, Arenaviridae, Bunyarviridae, Filoviridae, Orthomyxoviridae, Paramyxoviridae, Pneumoviridae, Rhabdoviridae, Retroviridae, and Hepadnaviridae, (2) bacteria of genera including, but not limited to, *Bacillus, Bartonella, Bordetella, Borre-*

*lia*, *Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*, (3) fungi of genera including, but not limited to, *Aspergillus, Candida, Cryptococcus, Histoplasma, Pneumocystis*, and *Stachybotrys*, and (4) protozoa and algae including, but not limited to, Prototheca wickerhami, *Plasmodium, Entamoeba, Giardia, Trypanosoma brucei, Toxoplasma gondii, Acanthamoeba, Leishmania, Babesia, Balamuthia mandrillaris, Cryptosporidium, Cyclospora*, and *Naegleria fowler.*

160. A method comprising providing a solution or kit of any one of the preceding embodiments; wherein a sample comprising nucleic acid is contacted with the solution; wherein the sample is collected from a subject suspected of being infected with SARS-CoV2.

161. A method comprising providing a solution or kit of any one of the preceding embodiments; wherein a sample comprising nucleic acid is contacted with the solution; wherein the sample is collected via nasopharyngeal swab.

162. A method comprising providing a solution or kit of any one of the preceding embodiments; wherein a sample comprising nucleic acid is contacted with the solution; wherein the sample is collected via nasopharyngeal swab and the sample is collected from a subject suspected of being infected with SARS-CoV2 or a subject desiring to be tested for a SARS-CoV2 infection.

163. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid.

164. A method, said method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the beads are isolated from the solution by one or more of exposure to a magnetic field, centrifugation or filtration, (3) the beads are washed and nucleic acid is subsequently eluted, and (4) the nucleic acid that was bound to the beads is analyzed for the presence or absence of pathogenic nucleic acid.

165. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the beads are isolated from the solution by one or more of exposure to a magnetic field, centrifugation or filtration, (3) the beads are washed and nucleic acid is subsequently eluted, and (4) the nucleic acid that was bound to the beads is analyzed for the presence or absence of pathogenic nucleic acid; wherein at least 30%; or at least 40%; or at least 50%; or at least 60%; or at least 70%; or at least 75%; or at least 80%; or at least 85%; or at least 90%; or at least 95% of the solution of step (1) that was contacted with the biological sample is used in step (2).

166. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the beads are isolated from the solution by one or more of exposure to a magnetic field, centrifugation or filtration, (3) the beads are washed and nucleic acid is subsequently eluted, and (4) the nucleic acid that was bound to the beads is analyzed for the presence or absence of pathogenic nucleic acid; wherein at least 30%; or at least 40%; or at least 50%; or at least 60%; or at least 70%; or at least 75%; or at least 80%; or at least 85%; or at least 90%; or at least 95% of the total nucleic of the original biological sample is still present after step (2).

167. A method comprising providing a solution of any one of the preceding embodiments; wherein the solution is contacted with a biological sample and wherein at least 30%; or at least 40%; or at least 50%; or at least 60%; or at least 70%; or at least 75%; or at least 80%; or at least 85%; or at least 90%; or at least 95% of the nucleic acid present in the biological sample is subjected to nucleic acid analysis.

168. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid; wherein steps (1) and (2) are performed without the use of a nucleic acid extraction solution other than the solution of step 1.

169. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid; wherein steps (1) and (2) are performed without the use of a nucleic acid extraction solution other than the solution of step 1.

170. A method comprising providing a solution of any one of the preceding embodiments having paramagnetic beads, wherein (1) a biological sample that has, or may have, nucleic acid from a pathogen is contacted with the solution such that the nucleic acid from the biological sample can bind to the paramagnetic beads, (2) the tube is exposed to a magnetic field to isolate the beads from the solution, (3) the beads are washed and nucleic acid is subsequently eluted, and (4) the nucleic acid that was bound to the beads is analyzed for the presence or absence of pathogenic nucleic acid; wherein steps 2, 3 and 4 are performed without the use of a nucleic acid extraction solution other than the solution of step 1 and wherein steps (1) and (2) are performed using a high-throughput nucleic acid processing and analysis system.
171. The composition or method of any one of the preceding embodiments wherein said sample or biological sample is from an animal.
172. The composition or method of any one of the preceding embodiments wherein said sample or biological sample is from a human subject.
173. The composition or method of any one of the preceding embodiments wherein said sample or biological sample is from a human subject, wherein said human subject is suspected of SARS-CoV2 virus or desires to be tested for the SARS-CoV2 virus.
174. The composition or method of any one of the preceding embodiments wherein said sample or biological sample is from a food product.
175. The composition or method of any one of the preceding embodiments wherein said sample or biological sample is an environmental sample.
176. The composition or method of any one of the preceding embodiments wherein solutions used do not include any guanidine salt (e.g., guanidine thiocyanate, guanidine isothiocyanate, guanidine HCl, or thiocyanic acid with guanidine).
177. The composition or method of any one of the preceding embodiments wherein solutions used do not include sodium iodide.
178. The composition or method of any one of the preceding embodiments wherein the solutions used do not include urea.
179. The composition or method of any one of the preceding embodiments with the proviso that the solutions do not include an alkaline solution.
180. The composition or method of any one of the preceding embodiments wherein solutions used do not include any enzyme selected from the group consisting of proteinase K, trypsin, dispase, collagenase, cellulase, chitinase, lysozyme, lipase, zymolase, and liticase.

The below Table A provides non-limiting examples of possible formulations of the disclosure; in addition to the specified components, each of the following solutions includes one or more antimicrobial agents as provided herein and paramagnetic beads as provided herein.

TABLE A

| | 1st Chelating Agent | 2nd Chelating Agent | 1st Detergent | 2nd Detergent | Salt | Cationic Polymer | pH Buffering Agent | Crowding Agent |
|---|---|---|---|---|---|---|---|---|
| Sv100 | EDTA, 125 mM | DFS, 100 μM | Cholate, 0.1% | DDM, 0.5% | NaCl, 1.5M | Poly-L-Lysine, <5 kDa, 50 μM | Phosphate pH7, 100 mM | PEG6000, 15% |
| Sv101 | EDTA, 62.5 mM | DFP, 250 μM | Cholate, 0.2% | NP-40, 0.5% | NaCl, 1.5M | Poly-L-Arginine, <70 kDa, 25 μM | Tris pH8, 250 mM | PEG6000, 18% |
| Sv102 | EGTA, 125 mM | DFM, 250 μM | Cholate, 0.3% | Triton X-100, 0.2% | NaCl, 1.5M | Poly-L-Lysine, <150 kDa, 12.5 μM | Tris pH8, 125 mM | PEG8000, 13% |
| Sv103 | EGTA, 62.5 mM | DFS, 200 μM | Cholate, 0.4% | Triton X-100, 1.0% | NaCl, 1.5M | Poly-L-Lysine, <300 kDa, 12.5 μM | HEPES pH7.5, 100 mM | PEG8000, 15% |
| Sv104 | EDTA, 50 mM | DFS, 100 μM | Cholate, 0.5% | Tween-20, 0.1% | NaCl, 1.5M | Poly-L-Lysine, <300 kDa, 12.5 μM | HEPES pH7.5, 200 mM | PEG8000, 18% |
| Sv105 | EDTA, 62.5 mM | DFP, 250 μM | Deoxycholate, 0.1% | DDM, 0.5% | NaCl, 1.5M | Poly-L-Arginine, <15 kDa, 150 μM | Phosphate pH7, 100 mM | PEG6000, 15% |
| Sv106 | EDTA, 125 mM | DFM, 250 μM | Deoxycholate, 0.2% | NP-40, 0.5% | NaCl, 1.5M | Poly-L-Lysine, <70 kDa, 12.5 μM | Tris pH8, 125 mM | PEG6000, 18% |
| Sv107 | EGTA, 62.5 mM | DFS, 200 μM | Deoxycholate, 0.3% | Triton X-100, 0.2% | NaCl, 1.5M | Poly-L-Lysine, <150 kDa, 25 μM | HEPES pH7.5, 100 mM | PEG8000, 15% |
| Sv108 | EGTA, 125 mM | DFM, 250 μM | Deoxycholate, 0.4% | Tween-20, 0.1% | NaCl, 1.5M | Poly-L-Lysine, <300 kDa, 12.5 μM | HEPES pH7.5, 200 mM | PEG8000, 18% |
| Sv109 | EDTA, 62.5 mM | DFM, 125 μM | SDS, .5% | Triton X, .5% | NaCl, 1.5M | Poly-L-Lysine, 12.5 μM | Tris pH8, 125 mM | PEG8000, 15% |
| Sv110 | EDTA, 62.5 mM | DFM, 125 μM | SDS, 0.5% | Triton X, .5% | NaCl, 1.5M | Poly-L-Lysine, <5 kDa, 12.5 μM | Tris pH8, 125 mM | PEG8000, 15% |
| Sv111 | EDTA, 125 mM | DFS, 100 μM | SDS, 0.1% | DDM, 0.5% | NaCl, 1.5M | Poly-L-Arginine, <15 kDa, 50 μM | Phosphate pH7, 100 mM | PEG6000, 15% |
| Sv112 | EGTA, 62.5 mM | DFP, 250 μM | SDS, 0.2% | NP-40, 0.5% | NaCl, 1.5M | Poly-L-Lysine, <70 kDa, 25 μM | Tris pH8, 250 mM | PEG6000, 18% |
| Sv113 | EGTA, 125 mM | DFM, 250 μM | SDS, 0.3% | Triton X-100, 0.2% | NaCl, 1.5M | Poly-L-Lysine, <150 kDa, 12.5 μM | HEPES pH7.5, 100 mM | PEG8000, 13% |
| Sv114 | EGTA, 62.5 mM | DFS, 200 μM | SDS, 0.7% | Triton X-100, 1.0% | NaCl, 1.5M | Poly-L-Lysine, <300 kDa, 125 μM | HEPES pH7.5, 200 mM | PEG8000, 15% |
| Sv115 | EDTA, 50 mM | DFS, 100 μM | SDS, 1.0% | Tween-20, 0.1% | NaCl, 1.5M | Poly-D-Lysine, <300 kDa, 150 μM | Phosphate pH7, 100 mM | PEG8000, 18% |
| Sv116 | EDTA, 62.5 mM | DFP, 250 μM | Sarkosyl, 0.5% | DDM, 0.5% | NaCl, 1.5M | Poly-L-Lysine, <5 kDa, 25 μM | Tris pH8, 125 mM | PEG6000, 15% |
| Sv117 | EDTA, 125 mM | DFM, 250 μM | Sarkosyl, 1.0% | NP-40, 0.5% | NaCl, 1.5M | Poly-L-Arginine, <70 kDa, 12.5 μM | Tris pH8, 250 mM | PEG6000, 18% |
| Sv118 | EGTA, 50 mM | DFS, 200 μM | Sarkosyl, 2.0% | Triton X-100, 0.2% | NaCl, 1.5M | Poly-L-Lysine, <150 kDa, 50 μM | Phosphate pH7, 100 mM | PEG8000, 13% |
| Sv119 | EGTA, 125 mM | DFM, 125 μM | Sarkosyl, 3.0% | Triton X-100, 1.0% | NaCl, 1.5M | Poly-L-Lysine, <300 kDa, 25 μM | HEPES pH7.5, 100 mM | PEG8000, 15% |
| Sv120 | EDTA, 62.5 mM | DFS, 100 μM | Sarkosyl, 5.0% | Tween-20, 0.1% | NaCl, 1.5M | Poly-D-Lysine, <300 kDa, 10 μM | HEPES pH7.5, 200 mM | PEG8000, 18% |
| Sv121 | EDTA, 100 mM | DFP, 250 μM | Deoxycholate, 0.5% | Tween-20, 0.1% | NaCl, 1.5M | Poly-L-Lysine, <70 kDa, 150 μM | Tris pH8, 250 mM | PEG8000, 15% |

TABLE A-continued

|  | 1st Chelating Agent | 2nd Chelating Agent | 1st Detergent | 2nd Detergent | Salt | Cationic Polymer | pH Buffering Agent | Crowding Agent |
|---|---|---|---|---|---|---|---|---|
| Sv122 | EDTA, 62.5 mM | DFP, 250 μM | Deoxycholate, 0.3% | DDM, 0.5% | LiCl, 1.5M | Poly-L-Lysine, <70 kDa, 150 μM | HEPES pH7.5, 100 mM | PEG6000, 15% |
| Sv123 | EGTA, 125 mM | DFM, 250 μM | SDS, 0.3% | DDM, 0.5% | LiCl, 1.5M | Poly-L-Lysine, <70 kDa, 12.5 μM | HEPES pH7.5, 100 mM | PEG6000, 15% |
| Sv124 | EGTA, 62.5 mM | DFS, 100 μM | Cholate, 0.4% | DDM, 0.5% | LiCl, 1.5M | Poly-L-Arginine, <15 kDa, 50 μM | HEPES pH7.5, 100 mM | PEG6000, 15% |
| Sv125 | EDTA, 50 mM | DFM, 250 μM | Cholate, 0.5% | NP-40, 0.5% | LiCl, 1.5M | Poly-L-Arginine, <70 kDa, 12.5 μM | HEPES pH7.5, 200 mM | PEG6000, 18% |
| Sv126 | EDTA, 62.5 mM | DFS, 100 μM | Deoxycholate, 0.4% | NP-40, 0.5% | LiCl, 1.5M | Poly-D-Lysine, <300 kDa, 12.5 μM | HEPES pH7.5, 200 mM | PEG6000, 18% |
| Sv127 | EDTA, 125 mM | DFS, 100 μM | SDS, 0.7% | NP-40, 0.5% | LiCl, 1.5M | Poly-D-Lysine, <300 kDa, 150 μM | HEPES pH7.5, 200 mM | PEG6000, 18% |
| Sv128 | EGTA, 62.5 mM | DFP, 250 μM | Sarkosyl, 3.0% | NP-40, 0.5% | LiCl, 1.5M | Poly-L-Arginine, <70 kDa, 25 μM | HEPES pH7.5, 100 mM | PEG6000, 18% |
| Sv129 | EGTA, 125 mM | DFP, 250 μM | Sarkosyl, 5.0% | Triton X-100, 0.2% | LiCl, 1.5M | Poly-L-Arginine, <15 kDa, 150 μM | HEPES pH7.5, 200 mM | PEG8000, 13% |
| Sv130 | EDTA, 100 mM | DFP, 250 μM | Deoxycholate, 0.1% | Triton X-100, 0.2% | LiCl, 1.5M | Poly-L-Lysine, <5 kDa, 25 μM | Phosphate pH7, 100 mM | PEG8000, 15% |
| Sv131 | EDTA, 62.5 mM | DFS, 100 μM | SDS, 0.1% | Triton X-100, 0.2% | LiCl, 1.5M | Poly-D-Lysine, <300 kDa, 10 μM | Phosphate pH7, 100 mM | PEG8000, 13% |
| Sv132 | EDTA, 125 mM | DFM, 250 μM | Sarkosyl, 2.0% | Triton X-100, 0.2% | LiCl, 1.5M | Poly-L-Lysine, <150 kDa, 12.5 μM | Phosphate pH7, 100 mM | PEG8000, 13% |
| Sv133 | EGTA, 50 mM | DFM, 250 μM | SDS, 1.0% | Tween-20, 0.1% | LiCl, 1.5M | Poly-L-Lysine, <300 kDa, 12.5 μM | Phosphate pH7, 100 mM | PEG8000, 18% |
| Sv134 | EGTA, 125 mM | DFM, 250 μM | Sarkosyl, 0.5% | Tween-20, 0.1% | LiCl, 1.5M | Poly-L-Lysine, <150 kDa, 12.5 μM | Tris pH8, 125 mM | PEG8000, 18% |
| Sv135 | EDTA, 62.5 mM | DFM, 125 μM | Deoxycholate, 0.2% | Tween-20, 0.1% | LiCl, 1.5M | Poly-L-Lysine, <300 kDa, 25 μM | Tris pH8, 125 mM | PEG8000, 15% |
| Sv136 | EDTA, 125 mM | DFS, 200 μM | Cholate, 0.3% | Tween-20, 0.1% | LiCl, 1.5M | Poly-L-Lysine, <150 kDa, 50 μM | Tris pH8, 125 mM | PEG8000, 18% |
| Sv137 | EGTA, 62.5 mM | DFS, 200 μM | Cholate, 0.2% | Tween-20, 0.1% | LiCl, 1.5M | Poly-L-Lysine, <300 kDa, 12.5 μM | Tris pH8, 250 mM | PEG8000, 18% |
| Sv138 | EGTA, 125 mM | DFS, 200 μM | Sarkosyl, 1.0% | Triton X-100, 1.0% | LiCl, 1.5M | Poly-L-Lysine, <150 kDa, 25 μM | Tris pH8, 250 mM | PEG8000, 15% |
| Sv139 | EGTA, 62.5 mM | DFP, 250 μM | SDS, 0.2% | Triton X-100, 1.0% | LiCl, 1.5M | Poly-L-Lysine, <70 kDa, 25 μM | Tris pH8, 250 mM | PEG8000, 15% |
| Sv140 | EDTA, 50 mM | DFS, 200 μM | Deoxycholate, 0.5% | Triton X-100, 1.0% | LiCl, 1.5M | Poly-L-Lysine, <300 kDa, 125 μM | Tris pH8, 250 mM | PEG8000, 15% |
| Sv141 | EDTA, 62.5 mM | DFM, 125 μM | SDS, 0.5% | Triton X, .5% | LiCl, 1.5M | Poly-L-Lysine, <5 kDa, 12.5 μM | Tris pH8, 125 mM | PEG8000, 15% |
| Sv142 | EDTA, 62.5 mM | DFP, 250 μM | Deoxycholate, 0.5% | Triton X-100, 0.2% | MgCl2, 1.5M | Poly-L-Arginine, <70 kDa, 25 μM | Tris pH8, 250 mM | PEG8000, 15% |
| Sv143 | EDTA, 62.5 mM | DFM, 250 μM | Deoxycholate, 0.2% | Triton X-100, 0.2% | MgCl2, 1.5M | Poly-L-Lysine, <150 kDa, 12.5 μM | Tris pH8, 125 mM | PEG8000, 13% |
| Sv144 | EDTA, 125 mM | DFS, 200 μM | SDS, 0.1% | Triton X-100, 1.0% | MgCl2, 1.5M | Poly-L-Lysine, <300 kDa, 12.5 μM | Phosphate pH7, 100 mM | PEG8000, 15% |
| Sv145 | EDTA, 62.5 mM | DFS, 100 μM | Sarkosyl, 1.0% | Tween-20, 0.1% | MgCl2, 1.5M | Poly-D-Lysine, <300 kDa, 12.5 μM | Tris pH8, 250 mM | PEG8000, 18% |
| Sv146 | EDTA, 125 mM | DFP, 250 μM | Cholate, 0.5% | Tween-20, 0.1% | MgCl2, 1.5M | Poly-L-Arginine, <15 kDa, 150 μM | HEPES pH7.5, 200 mM | PEG8000, 18% |
| Sv147 | EDTA, 125 mM | DFM, 250 μM | SDS, 1.0% | Triton X-100, 1.0% | MgCl2, 1.5M | Poly-L-Lysine, <70 kDa, 12.5 μM | Phosphate pH7, 100 mM | PEG8000, 15% |
| Sv148 | EGTA, 62.5 mM | DFS, 200 μM | Cholate, 0.2% | Triton X-100, 1.0% | MgCl2, 1.5M | Poly-L-Lysine, <150 kDa, 25 μM | Tris pH8, 250 mM | PEG8000, 15% |
| Sv149 | EGTA, 125 mM | DFM, 250 μM | Deoxycholate, 0.1% | Tween-20, 0.1% | MgCl2, 1.5M | Poly-L-Lysine, <300 kDa, 12.5 μM | Phosphate pH7, 100 mM | PEG8000, 18% |
| Sv150 | EGTA, 62.5 mM | DFP, 250 μM | Sarkosyl, 0.5% | DDM, 0.5% | MgCl2, 1.5M | Poly-L-Lysine, <70 kDa, 150 μM | Tris pH8, 125 mM | PEG6000, 15% |
| Sv151 | EGTA, 50 mM | DFP, 250 μM | Sarkosyl, 5.0% | DDM, 0.5% | MgCl2, 1.5M | Poly-L-Lysine, <5 kDa, 25 μM | HEPES pH7.5, 200 mM | PEG6000, 15% |
| Sv152 | EGTA, 125 mM | DFM, 250 μM | Cholate, 0.3% | Triton X-100, 0.2% | MgCl2, 1.5M | Poly-L-Arginine, <70 kDa, 12.5 μM | Tris pH8, 125 mM | PEG8000, 13% |
| Sv153 | EDTA, 50 mM | DFS, 200 μM | Deoxycholate, 0.4% | Tween-20, 0.1% | MgCl2, 1.5M | Poly-L-Lysine, <150 kDa, 50 μM | HEPES pH7.5, 200 mM | PEG8000, 18% |
| Sv154 | EGTA, 125 mM | DFM, 125 μM | SDS, 0.3% | DDM, 0.5% | MgCl2, 1.5M | Poly-L-Lysine, <300 kDa,25 μM | HEPES pH7.5, 100 mM | PEG6000, 15% |
| Sv155 | EDTA, 100 mM | DFS, 100 μM | Sarkosyl, 3.0% | NP-40, 0.5% | MgCl2, 1.5M | Poly-D-Lysine, <300 kDa, 10 μM | HEPES pH7.5, 100 mM | PEG6000, 18% |
| Sv156 | EDTA, 62.5 mM | DFS, 100 μM | Sarkosyl, 2.0% | Triton X-100, 0.2% | MgCl2, 1.5M | Poly-L-Arginine, <15 kDa, 50 μM | Phosphate pH7, 100 mM | PEG8000, 13% |
| Sv157 | EDTA, 50 mM | DFP, 250 μM | Cholate, 0.4% | NP-40, 0.5% | MgCl2, 1.5M | Poly-L-Lysine, <70 kDa, 25 μM | HEPES pH7.5, 100 mM | PEG6000, 18% |
| Sv158 | EGTA, 62.5 mM | DFM, 250 μM | Deoxycholate, 0.3% | NP-40, 0.5% | MgCl2, 1.5M | Poly-L-Lysine, <150 kDa, 12.5 μM | HEPES pH7.5, 100 mM | PEG6000, 18% |
| Sv159 | EGTA, 125 mM | DFS, 200 μM | SDS, 0.2% | NP-40, 0.5% | MgCl2, 1.5M | Poly-L-Lysine, <300 kDa, 125 μM | Tris pH8, 250 mM | PEG6000, 18% |

TABLE A-continued

| | 1st Chelating Agent | 2nd Chelating Agent | 1st Detergent | 2nd Detergent | Salt | Cationic Polymer | pH Buffering Agent | Crowding Agent |
|---|---|---|---|---|---|---|---|---|
| Sv160 | EGTA, 62.5 mM | DFS, 100 μM | SDS, 0.7% | Tween-20, 0.1% | MgCl2, 1.5M | Poly-D-Lysine, <300 kDa, 150 μM | HEPES pH7.5, 200 mM | PEG8000, 15% |
| Sv161 | EDTA, 62.5 mM | DFM, 125 μM | SDS, 0.5% | Triton X, .5% | MgCl2, 1.5M | Poly-L-Lysine, <5 kDa, 12.5 μM | Tris pH8, 125 mM | PEG8000, 15% |
| Sv162 | EGTA, 62.5 mM | DFP, 250 μM | Cholate, 0.2% | Tween-20, 0.1% | Na2SO4, 1.5M | Poly-L-Arginine, <15 kDa, 150 μM | Tris pH8, 250 mM | PEG8000, 15% |
| Sv163 | EGTA, 125 mM | DFP, 250 μM | Cholate, 0.3% | NP-40, 0.5% | Na2SO4, 1.5M | Poly-L-Lysine, <5 kDa, 25 μM | Tris pH8, 125 mM | PEG6000, 18% |
| Sv164 | EGTA, 62.5 mM | DFS, 100 μM | Cholate, 0.4% | DDM, 0.5% | Na2SO4, 1.5M | Poly-L-Arginine, <15 kDa, 50 μM | HEPES pH7.5, 100 mM | PEG6000, 15% |
| Sv165 | EDTA, 50 mM | DFP, 250 μM | Cholate, 0.5% | NP-40, 0.5% | Na2SO4, 1.5M | Poly-L-Arginine, <70 kDa, 25 μM | HEPES pH7.5, 200 mM | PEG6000, 18% |
| Sv166 | EGTA, 125 mM | DFM, 250 μM | Deoxycholate, 0.1% | Tween-20, 0.1% | Na2SO4, 1.5M | Poly-L-Lysine, <70 kDa, 12.5 μM | Phosphate pH7, 100 mM | PEG8000, 18% |
| Sv167 | EGTA, 62.5 mM | DFM, 250 μM | Deoxycholate, 0.2% | Tween-20, 0.1% | Na2SO4, 1.5M | Poly-L-Arginine, <70 kDa, 12.5 μM | Tris pH8, 125 mM | PEG8000, 18% |
| Sv168 | EGTA, 125 mM | DFP, 250 μM | Deoxycholate, 0.3% | NP-40, 0.5% | Na2SO4, 1.5M | Poly-L-Lysine, <70 kDa, 12.5 μM | HEPES pH7.5, 100 mM | PEG6000, 18% |
| Sv169 | EDTA, 62.5 mM | DFM, 250 μM | Deoxycholate, 0.4% | DDM, 0.5% | Na2SO4, 1.5M | Poly-L-Lysine, <150 kDa, 12.5 μM | HEPES pH7.5, 200 mM | PEG6000, 15% |
| Sv170 | EDTA, 62.5 mM | DFS, 200 μM | Deoxycholate, 0.5% | DDM, 0.5% | Na2SO4, 1.5M | Poly-L-Lysine, <150 kDa, 25 μM | Tris pH8, 250 mM | PEG6000, 15% |
| Sv171 | EDTA, 125 mM | DFS, 200 μM | Sarkosyl, 0.5% | Tween-20, 0.1% | Na2SO4, 1.5M | Poly-L-Lysine, <150 kDa, 50 μM | Tris pH8, 125 mM | PEG8000, 18% |
| Sv172 | EGTA, 50 mM | DFM, 250 μM | Sarkosyl, 1.0% | Triton X-100, 0.2% | Na2SO4, 1.5M | Poly-L-Lysine, <150 kDa, 12.5 μM | Tris pH8, 250 mM | PEG8000, 13% |
| Sv173 | EDTA, 50 mM | DFS, 100 μM | Sarkosyl, 2.0% | Tween-20, 0.1% | Na2SO4, 1.5M | Poly-D-Lysine, <300 kDa, 12.5 μM | Phosphate pH7, 100 mM | PEG8000, 18% |
| Sv174 | EDTA, 62.5 mM | DFM, 250 μM | Sarkosyl, 3.0% | Triton X-100, 0.2% | Na2SO4, 1.5M | Poly-L-Lysine, <300 kDa, 12.5 μM | HEPES pH7.5, 100 mM | PEG8000, 13% |
| Sv175 | EDTA, 125 mM | DFP, 250 μM | Sarkosyl, 5.0% | Triton X-100, 1.0% | Na2SO4, 1.5M | Poly-L-Lysine, <70 kDa, 150 μM | HEPES pH7.5, 200 mM | PEG8000, 15% |
| Sv176 | EGTA, 125 mM | DFS, 100 μM | SDS, 0.1% | Triton X-100, 0.2% | Na2SO4, 1.5M | Poly-D-Lysine, <300 kDa, 10 μM | Phosphate pH7, 100 mM | PEG8000, 13% |
| Sv177 | EDTA, 62.5 mM | DFS, 100 μM | SDS, 0.2% | Triton X-100, 1.0% | Na2SO4, 1.5M | Poly-D-Lysine, <300 kDa, 150 μM | Tris pH8, 250 mM | PEG8000, 15% |
| Sv178 | EDTA, 125 mM | DFS, 200 μM | SDS, 0.3% | Triton X-100, 0.2% | Na2SO4, 1.5M | Poly-L-Lysine, <300 kDa, 12.5 μM | HEPES pH7.5, 100 mM | PEG8000, 15% |
| Sv179 | EGTA, 62.5 mM | DFM, 125 μM | SDS, 0.7% | NP-40, 0.5% | Na2SO4, 1.5M | Poly-L-Lysine, <300 kDa, 25 μM | HEPES pH7.5, 200 mM | PEG6000, 18% |
| Sv180 | EDTA, 100 mM | DFS, 200 μM | SDS, 1.0% | Triton X-100, 1.0% | Na2SO4, 1.5M | Poly-L-Lysine, <300 kDa, 125 μM | Phosphate pH7, 100 mM | PEG8000, 15% |
| Sv181 | EDTA, 62.5 mM | DFM, 125 μM | SDS, 0.5% | Triton X, .5% | Na2SO4, 1.5M | Poly-L-Lysine, <5 kDa, 12.5 μM | Tris pH8, 125 mM | PEG8000, 15% |
| Sv182 | EDTA, 100 mM | DFS, 200 μM | Deoxycholate, 0.1% | NP-40, 0.5% | KCl, 1.5M | Poly-L-Lysine, <150 kDa, 25 μM | Phosphate pH7, 100 mM | PEG6000, 18% |
| Sv183 | EDTA, 125 mM | DFM, 250 μM | Sarkosyl, 0.5% | Triton X-100, 0.2% | KCl, 1.5M | Poly-L-Lysine, <150 kDa, 12.5 μM | Tris pH8, 125 mM | PEG8000, 13% |
| Sv184 | EDTA, 125 mM | DFS, 200 μM | SDS, 0.1% | Triton X-100, 1.0% | KCl, 1.5M | Poly-L-Lysine, <300 kDa, 12.5 μM | Phosphate pH7, 100 mM | PEG8000, 15% |
| Sv185 | EDTA, 125 mM | DFS, 100 μM | Cholate, 0.2% | Tween-20, 0.1% | KCl, 1.5M | Poly-L-Lysine, <300 kDa, 12.5 μM | Tris pH8, 250 mM | PEG8000, 18% |
| Sv186 | EDTA, 50 mM | DFM, 250 μM | Deoxycholate, 0.2% | DDM, 0.5% | KCl, 1.5M | Poly-L-Lysine, <300 kDa, 12.5 μM | Tris pH8, 125 mM | PEG6000, 15% |
| Sv187 | EDTA, 50 mM | DFS, 200 μM | Sarkosyl, 1.0% | NP-40, 0.5% | KCl, 1.5M | Poly-L-Lysine, <300 kDa, 125 μM | Tris pH8, 250 mM | PEG8000, 18% |
| Sv188 | EDTA, 62.5 mM | DFM, 125 μM | SDS, 0.2% | Triton X-100, 0.2% | KCl, 1.5M | Poly-L-Lysine, <300 kDa, 25 μM | Tris pH8, 250 mM | PEG8000, 15% |
| Sv189 | EDTA, 62.5 mM | DFS, 100 μM | Cholate, 0.3% | Tween-20, 0.1% | KCl, 1.5M | Poly-D-Lysine, <300 kDa, 10 μM | Tris pH8, 125 mM | PEG8000, 18% |
| Sv190 | EDTA, 62.5 mM | DFP, 250 μM | Deoxycholate, 0.3% | Tween-20, 0.1% | KCl, 1.5M | Poly-L-Arginine, <15 kDa, 150 μM | HEPES pH7.5, 100 mM | PEG8000, 15% |
| Sv191 | EDTA, 62.5 mM | DFS, 100 μM | Sarkosyl, 2.0% | DDM, 0.5% | KCl, 1.5M | Poly-L-Arginine, <15 kDa, 50 μM | Phosphate pH7, 100 mM | PEG6000, 15% |
| Sv192 | EGTA, 125 mM | DFS, 200 μM | SDS, 0.3% | NP-40, 0.5% | KCl, 1.5M | Poly-L-Lysine, <150 kDa, 50 μM | HEPES pH7.5, 100 mM | PEG8000, 18% |
| Sv193 | EGTA, 125 mM | DFS, 100 μM | Cholate, 0.5% | Triton X-100, 0.2% | KCl, 1.5M | Poly-D-Lysine, <300 kDa, 150 μM | HEPES pH7.5, 200 mM | PEG8000, 13% |
| Sv194 | EGTA, 125 mM | DFP, 250 μM | Deoxycholate, 0.4% | Triton X-100, 1.0% | KCl, 1.5M | Poly-L-Lysine, <5 kDa, 25 μM | HEPES pH7.5, 200 mM | PEG8000, 15% |
| Sv195 | EGTA, 125 mM | DFM, 250 μM | Deoxycholate, 0.5% | Tween-20, 0.1% | KCl, 1.5M | Poly-L-Lysine, <70 kDa, 12.5 μM | Tris pH8, 250 mM | PEG8000, 18% |
| Sv196 | EGTA, 50 mM | DFM, 250 μM | Sarkosyl, 5.0% | DDM, 0.5% | KCl, 1.5M | Poly-L-Lysine, <150 kDa, 12.5 μM | HEPES pH7.5, 200 mM | PEG6000, 15% |
| Sv197 | EGTA, 62.5 mM | DFP, 250 μM | SDS, 1.0% | NP-40, 0.5% | KCl, 1.5M | Poly-L-Arginine, <70 kDa, 25 μM | Phosphate pH7, 100 mM | PEG6000, 18% |

TABLE A-continued

| | 1st Chelating Agent | 2nd Chelating Agent | 1st Detergent | 2nd Detergent | Salt | Cationic Polymer | pH Buffering Agent | Crowding Agent |
|---|---|---|---|---|---|---|---|---|
| Sv198 | EGTA, 62.5 mM | DFM, 250 µM | Cholate, 0.4% | Triton X-100, 0.2% | KCl, 1.5M | Poly-L-Arginine, <70 kDa, 12.5 µM | HEPES pH7.5, 100 mM | PEG8000, 13% |
| Sv199 | EGTA, 62.5 mM | DFP, 250 µM | Sarkosyl, 3.0% | Triton X-100, 1.0% | KCl, 1.5M | Poly-L-Lysine, <70 kDa, 25 µM | HEPES pH7.5, 100 mM | PEG8000, 15% |
| Sv200 | EGTA, 62.5 mM | DFP, 250 µM | SDS, 0.7% | Tween-20, 0.1% | KCl, 1.5M | Poly-L-Lysine, <70 kDa, 150 µM | HEPES pH7.5, 200 mM | PEG8000, 18% |
| Sv201 | EDTA, 62.5 mM | DFM, 125 µM | SDS, 0.5% | Triton X, .5% | KCl, 1.5M | Poly-L-Lysine, <5 kDa, 12.5 µM | Tris pH8, 125 mM | PEG8000, 15% |

The inventions illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present inventions have been specifically disclosed by preferred embodiments and optional features, modification and variation of the concepts herein disclosed may be resorted to by those skilled in the art, and that such modifications and variations are considered to be within the scope of the inventions as defined by the appended embodiments and elsewhere in the disclosure.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The term "about" as used herein means in quantitative terms plus or minus 10%. For example, "About 3%" would encompass 2.7-3.3% and "About 10%" would encompass 9-11%". Moreover, where "about" is used herein in conjunction with a quantitative term it is understood that in addition to the value plus or minus 10%, the exact value of the quantitative term is also contemplated and described—for example, the term "about 3%" expressly contemplates, describes and includes exactly 3%.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of various aspects and embodiments of inventions contemplated herein.

Certain aspects and embodiments of inventions have been described broadly and generically herein. Each of the narrower species and subgeneric groupings falling within the generic disclosure also form part of some aspects and embodiments of inventions contemplated herein. This includes the generic description of inventions with a proviso or negative limitation removing any subject matter from the genus, regardless of whether or not the excised material is specifically recited herein.

In addition, where features or aspects of the invention are described in terms of Markush groups, those skilled in the art will recognize that some aspects and embodiments of inventions contemplated herein are also thereby described in terms of any individual member or subgroup of members of the Markush group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following embodiments define the scope of the invention and that methods and structures within the scope of these embodiments and their equivalents be covered thereby.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

All publications, patents, and patent applications mentioned in this specification are herein incorporated by reference to the same extent as if each individual publication, patent, or patent application was specifically and individually indicated to be incorporated by reference. In the case of conflict, the specification, including definitions, will control.

EXAMPLES

Example 1

Preparation of an EPM-IX Solution

An EPM-IX solution is made by making a solution having the components and amounts of a solution listed on Table A.

The EPM-IX solution further has paramagnetic beads in a concentration of 100 mg/L; wherein the beads are "Speedbeads" with a 60% magnate content and having an average diameter of 1 μm.

Example 2

Comparison of EPM-IX to Viral Transport Media (VTM) with Immediate Extraction

SARS-CoV2 positive-control (ZeptoMetrix) was diluted directly into 1 ml of EMP-IX or VTM, mixed by vortexing for 10 sec, and incubated for 20 minutes at room temperature. VTM samples were extracted using the QIAamp Viral RNA Mini Kit (Qiagen) according to CDC protocol (CDC-006-00019) recommendation of 100 ul for extraction and 100 ul for elution. Viral RNA yields were assessed using the CDC 2019-Novel Coronavirus (2019-nCoV) Real-Time RT-PCR Diagnostic Panel and are show in FIG. 1 and Table 1. Ct values are for both probes N1 and N2. Note that Ct differentials exist on a loge-scale, so that a Ct difference of 1 equals a yield difference of 2-fold and a Ct difference of 2 equals a yield difference of 4-fold.

TABLE 1a

Convergent Enhanced Preservation Media (EPM-IX); N1 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 25.0 | 26.8 | 25.6 | 26.7 | 26.0 | 0.9 |
| 3 | 29.1 | 27.5 | 29.9 | 28.6 | 28.8 | 1.0 |

TABLE 1b

CDC Viral Transport Media (VTM); N1 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 32.0 | 29.4 | 30.5 | 30.0 | 30.5 | 1.1 |
| 3 | 35.1 | 35.0 | 31.3 | 34.3 | 33.9 | 1.8 |

TABLE 1c

Convergent Enhanced Preservation Media (EPM-IX); N2 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 25.9 | 26.8 | 25.5 | 26.6 | 26.2 | 0.6 |
| 3 | 29.0 | 26.1 | 29.3 | 28.5 | 28.2 | 1.4 |

TABLE 1d

CDC Viral Transport Media (VTM); N2 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 32.1 | 29.7 | 30.6 | 30.1 | 30.6 | 1.1 |
| 3 | 35.1 | 35.6 | 31.7 | 34.7 | 34.3 | 1.7 |

TABLE 1e $\Delta Ct\ (Ct^{VTM} - Ct^{EPM})$; [Fold improvement]

| SARS-CoV2 (ul) | N1 | N2 |
|---|---|---|
| 15 | 4.5 [23x] | 4.4 [21x] |
| 3 | 5.1 [34x] | 6.1 [69x] |

Example 3

Comparison of EPM-IX to Viral Transport Media (VTM) Following 24 HR Incubation

Figure 2:
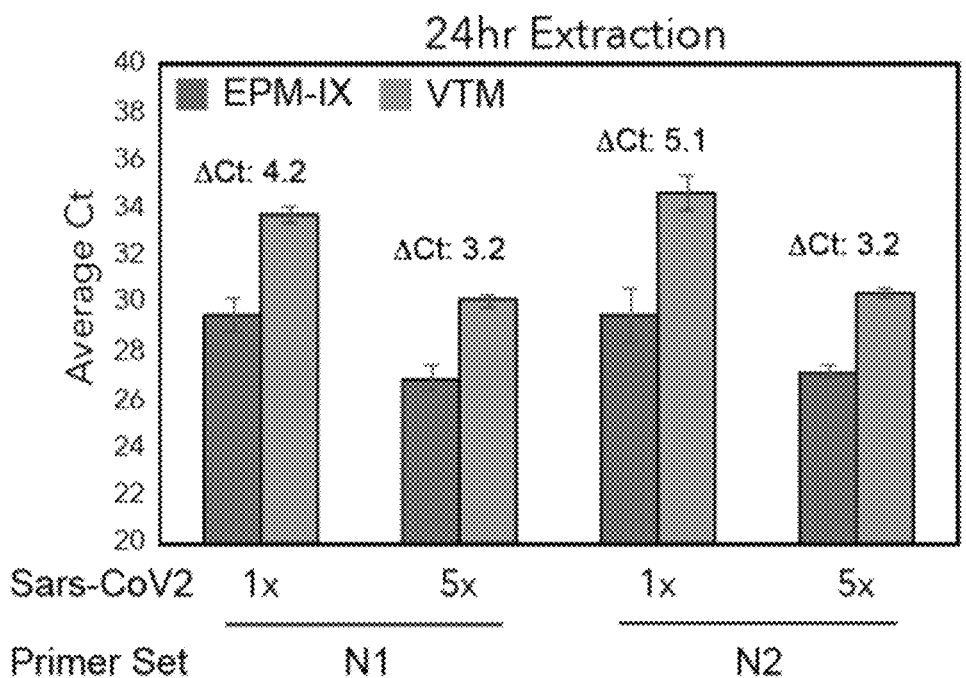
FIG. 2 illustrates an increase in repeatability and stability of the sample in the Enhanced Preservation Media as compared to Viral Transport Media after extraction 24 hours following exposure to the sample.

SARS-CoV2 positive-control (ZeptoMetrix) was diluted directly into 1 ml of EMP-IX or VTM, mixed by vortexing for 10 sec, and incubated for 24 hrs at room temperature. VTM samples were extracted using the QIAamp Viral RNA Mini Kit (Qiagen) according to CDC protocol (CDC-006-00019) recommendation of 100 ul for extraction and 100 ul for elution. Viral RNA yields were assessed using the CDC 2019-Novel Coronavirus (2019-nCoV) Real-Time RT-PCR Diagnostic Panel and are shown graphically in FIG. 2. Ct values for probes N1 and N2. Note that Ct differentials exist on a loge-scale, so that a Ct difference of 1 equals a yield difference of 2-fold and a Ct difference of 2 equals a yield difference of 4-fold.

TABLE 2a

Convergent Enhanced Preservation Media (EPM-IX); N1 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 27.3 | 26.2 | 27.1 | 27.0 | 26.9 | 0.5 |
| 3 | 28.6 | 29.5 | 30.3 | 29.4 | 29.5 | 0.7 |

TABLE 2b

CDC Viral Transport Media (VTM); N1 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 30.4 | 29.9 | 29.9 | 30.0 | 30.1 | 0.3 |
| 3 | 33.6 | 33.5 | 34.0 | 33.6 | 33.7 | 0.3 |

TABLE 2c

Convergent Enhanced Preservation Media (EPM-IX); N2 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 27.1 | 27.6 | 27.0 | 27.1 | 27.2 | 0.3 |
| 3 | 28.1 | 29.8 | 30.8 | 29.3 | 29.5 | 1.1 |

TABLE 2d

CDC Viral Transport Media (VTM); N2 probe

| SARS-CoV2 (ul) | Rep 1 (Ct) | Rep 2 (Ct) | Rep 3 (Ct) | Rep 4 (Ct) | Average (Ct) | SD (Ct) |
|---|---|---|---|---|---|---|
| 15 | 30.4 | 30.1 | 30.3 | 30.6 | 30.4 | 0.2 |
| 3 | 34.7 | 33.9 | 35.5 | 34.2 | 34.6 | 0.7 |

TABLE 2e $\Delta$Ct (Ct$^{VTM}$-Ct$^{EPM}$); [Fold improvement]

| SARS-CoV2 (ul) | N1 | N2 |
|---|---|---|
| 15 | 3.2 [9x] | 3.2 [9x] |
| 3 | 4.2 [18x] | 5.1 [34x] |

Example 4

EPM-IX Performance Time-Course at Room Temperature

Figure 3:
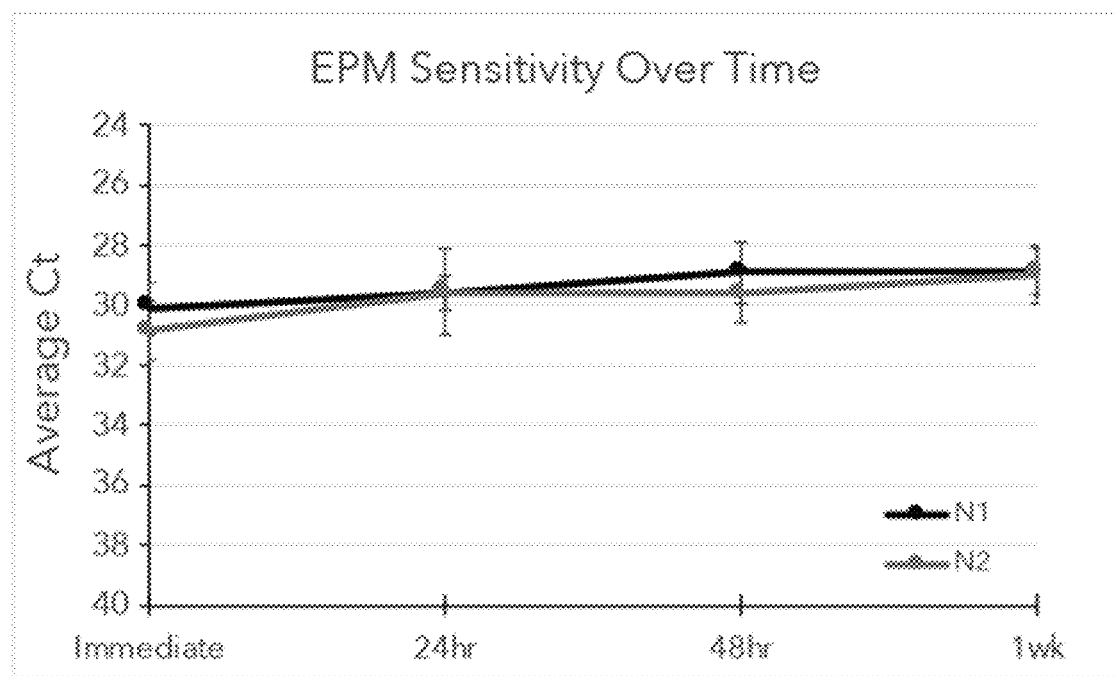
FIG. 3 illustrates sample stability within the Enhanced Preservation Media after up to 1 week of initial collection.

SARS-CoV2 positive-control (ZeptoMetrix) was diluted directly into 1 ml of EPM-IX, mixed by vortexing for 10 sec, and incubated at room temperature for a time-course up to 1 week. 3 ul of ZeptoMetrix control was added to each tube, and incubations, extractions, and PCR were performed in triplicate. Viral RNA yields were assessed using the CDC 2019-Novel Coronavirus (2019-nCoV) Real-Time RT-PCR Diagnostic Panel and are represented graphically in FIG. 3. Ct values for probes N1 and N2 are reported.

TABLE 3a

Immediate

| SARS-CoV2 Probe | Rep 1 (Ct) | Rep 2 (Ct) | Rep 3 (Ct) | Average (Ct) | SD (Ct) |
|---|---|---|---|---|---|
| N1 | 31.1 | 29.3 | 30.0 | 30.1 | 0.9 |
| N2 | 31.9 | 30.2 | 30.5 | 30.8 | 1.0 |

TABLE 3b 24 hours

| SARS-CoV2 Probe | Rep 1 (Ct) | Rep 2 (Ct) | Rep 3 (Ct) | Average (Ct) | SD (Ct) |
|---|---|---|---|---|---|
| N1 | 29.0 | 30.1 | 29.7 | 29.6 | 0.5 |
| N2 | 27.9 | 30.6 | 30.2 | 29.6 | 1.4 |

TABLE 3c 48 hours

| SARS-CoV2 Probe | Rep 1 (Ct) | Rep 2 (Ct) | Rep 3 (Ct) | Average (Ct) | SD (Ct) |
|---|---|---|---|---|---|
| N1 | 28.6 | 30.1 | 28.1 | 28.9 | 1.1 |
| N2 | 29.2 | 30.7 | 29.0 | 29.6 | 0.9 |

TABLE 3d 1 week

| SARS-CoV2 Probe | Rep 1 (Ct) | Rep 2 (Ct) | Rep 3 (Ct) | Average (Ct) | SD (Ct) |
|---|---|---|---|---|---|
| N1 | 29.3 | 28.0 | 29.3 | 28.9 | 0.8 |
| N2 | 30.1 | 28.6 | 28.2 | 29.0 | 1.0 |

Example 5

EPM-IX Performance Under Extreme Summer Shipping Conditions

Figure 4:
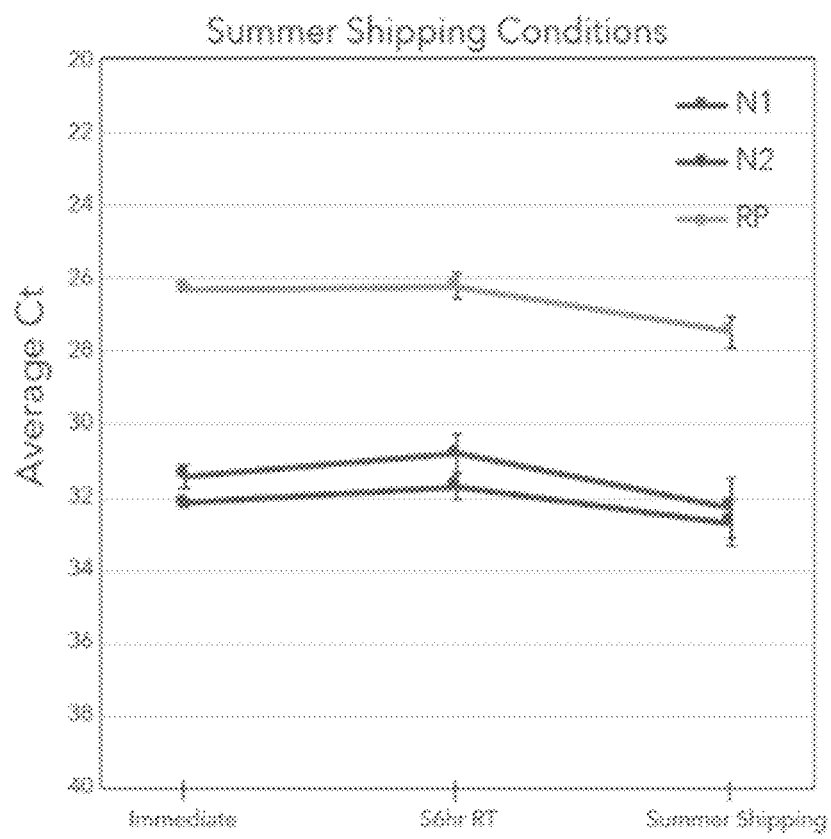
FIG. 4 illustrates sample stability within the Enhanced Preservation Media after exposure to standard shipping conditions.

A mid-turbinate swab was collected into 1 ml of EPM-IX and mixed by vortexing. Then 10 ul of SARS-CoV2 positive-control (ZeptoMetrix) was added to the EMP-IX mix and vortexed for 10 sec. The 1 ml sample was then split into 100 ul aliquots; 3 aliquots were immediately extracted, 3 aliquots were incubated at RT for the full 56 hr time-course, and 3 were added to a PCR block and subjected to the Summer Shipping time-course outlined in Table 4a. Average Ct results are shown in FIG. 4.

TABLE 4a

| Temperature | Cycle Period | Cycle Period Hours | Total Time Hours |
|---|---|---|---|
| 40° C. | 1 | 8 | 8 |
| 22° C. | 2 | 4 | 12 |
| 40° C. | 3 | 2 | 14 |
| 30° C. | 4 | 36 | 50 |
| 40° C. | 5 | 6 | 56 |

Viral and control RNA yields were assessed using the CDC 2019-Novel Coronavirus (2019-nCoV) Real-Time RT-PCR Diagnostic Panel. Ct values for probes N1, N2, and RP are reported in Table 4b-d.

TABLE 4b

Immediate Extraction

| SARS-CoV2 (ul) | Rep 1 (Ct) | Rep 2 (Ct) | Rep 3 (Ct) | Average (Ct) | SD (Ct) |
|---|---|---|---|---|---|
| N1 | 31.6 | 31.5 | 31.0 | 31.4 | 0.3 |
| N2 | 32.1 | 32.1 | 32.3 | 32.1 | 0.1 |
| RP | 26.2 | 26.3 | 26.3 | 26.3 | 0.1 |

TABLE 4c 56 hr RT Incubation

| SARS-CoV2 (ul) | Rep 1 (Ct) | Rep 2 (Ct) | Rep 3 (Ct) | Average (Ct) | SD (Ct) |
|---|---|---|---|---|---|
| N1 | 30.8 | 30.3 | 31.3 | 30.8 | 0.5 |
| N2 | 31.7 | 31.3 | 32.0 | 31.7 | 0.4 |
| RP | 26.4 | 25.8 | 26.5 | 26.2 | 0.4 |

TABLE 4d

| Summer Shipping Incubation | | | | | |
|---|---|---|---|---|---|
| SARS-CoV2 (ul) | Rep 1 (Ct) | Rep 2 (Ct) | Rep 3 (Ct) | Average (Ct) | SD (Ct) |
| N1 | 31.3 | 32.7 | 32.7 | 32.2 | 0.8 |
| N2 | 32.0 | 32.7 | 33.3 | 32.7 | 0.7 |
| RP | 27.8 | 27.0 | 27.6 | 27.5 | 0.4 |

Example 6

Testing EPM-IX Sample Washing Conditions

Volunteers performed mid-turbinate swabbing into EPM-IX test collection tubes. Samples were split into two equal fractions and each extracted with the same protocol except for EtOH wash condition. After bead clarification/magnetic binding from EPM-IX and complete removal of supernatant, the following washes were performed:

Double Wash: 800 ul of 80% EtOH is added, removed from magnet, mixed by pipet, and returned to the magnet for clarification. The first wash is removed in its entirety and a second EtOH wash is performed with the tubes remaining on the magnet. Following the second wash, samples are dried for 5 minutes and resuspended in H2O.

Single Wash: Following magnetic binding and removal of EPM supernatant, 800 ul of 80% EtOH is added to the tube and then removed after 30 seconds, aspirating all EtOH wash. Tubes are never removed from the magnet. Sample are dried for 5 minutes and resuspended in H2O.

Figure 5:
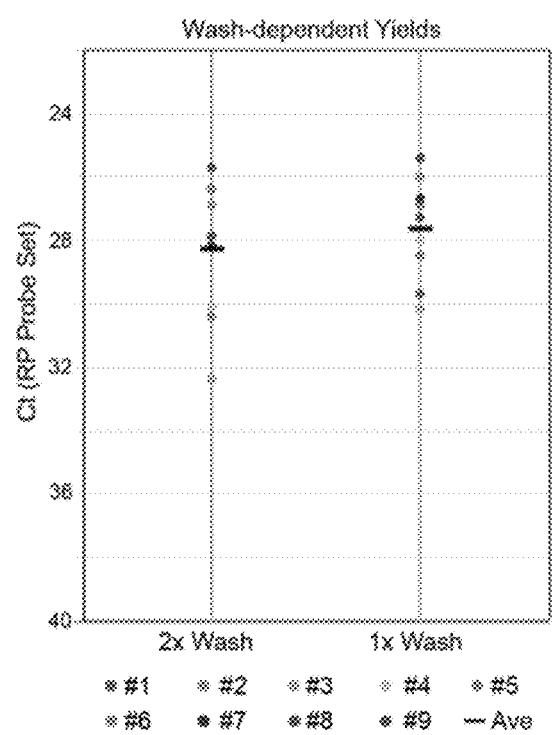
FIG. 5 illustrates the efficacy for the integrated extraction aspect of the Enhanced Preservation Media for use in high-throughput screening protocols.

RNA yields were assessed using the CDC 2019-Novel Coronavirus (2019-nCoV) Real-Time RT-PCR Diagnostic Panel and are represented in FIG. 5. Ct values for probe RP are reported.

TABLE 5

| SARS-CoV-2 Probe | Double Wash | Single on Bead Wash |
|---|---|---|
| Sample 1 | 26.4 | 29.7 |
| Sample 2 | 26.9 | 26.0 |
| Sample 3 | 32.4 | 30.2 |
| Sample 4 | 30.1 | 28 |
| Sample 5 | 30.4 | 28.5 |
| Sample 6 | 26.4 | 26.9 |
| Sample 7 | 28.2 | 26.7 |
| Sample 8 | 25.7 | 25.4 |
| Sample 9 | 27.9 | 27.3 |
| Average | 28.3 | 27.6 |

Example 7

EPM Protects Nucleic Acids by Physically Restricting Access to the Molecule

Figure 6:
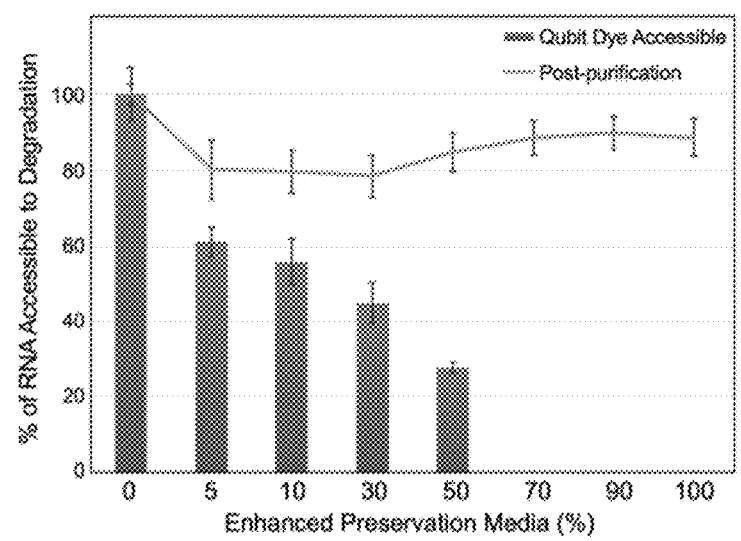
FIG. 6 illustrates the ability of the Enhanced Preservation Media to protect the sample from degradation.

Purified RNA was diluted in increasing concentrations of EPM that did not contain the integrated extraction components of EPM-IX (i.e., detergents, crowding agent, and magnetic beads) and measured using the Qubit HS RNA kit (Blue bars). RNA in EPM was then subjected to AMPure bead purification, eluted in H2O, and measured again by Qubit (Yellow line). Both assays were performed in triplicate and are presented in FIG. 6.

Example 8

Sample Processing Procedure Following Specimen Collection

I. Procedure
  A. Sample Preparation
    1. Obtain samples stored at RT.
  B. If samples are refrigerated, allow samples to sit at RT for 30 minutes until samples have warmed to RT. Reagent Preparation
    1. Prepare 80% Ethanol
      a. Combine eight parts of molecular grade ethanol with two parts of molecular grade water. 40 mL molecular grade ethanol with 10 mL molecular grade water combined in a 50 mL tube.
  C. Purification
    1. Mix sample collection tubes by pulse vortexing for 3-5 seconds.
    2. For viruses, proceed to step 4. For pathogens with a cell wall, cap tubes and place in an incubator at 95° C. for 15 minutes.
      a. Allow tubes to return to RT.
      b. Pulse vortex tubes 5 seconds.
      c. Spin briefly in a minicentrifuge to bring down sample contents from the lid or side of the tube.
      d. Proceed to step 4.
    3. Place the tubes on the DynaMag magnetic stand and incubate at RT for 10 minutes to allow the beads to separate from the solution.
    4. Withdraw supernatant with P1000 pipette. Observe caution to avoid disturbing the beads.
    5. With tubes still on the magnet, pipette 900 µL of 80% EtOH to each tube and let sit for 30 seconds.
    6. Repeats steps 4 and 5 for a second wash.
    7. Spin each tube briefly in a mini centrifuge to bring down the contents of any sample in the lid or side of the tube.
    8. Withdraw and discard the supernatant with a P1000 without disturbing the beads.
    9. Using P20 pipette, carefully remove all remnant EtOH at the bottom of the tube.
    10. Air-dry the beads at RT for 1-3 minutes with the caps open while the tubes are still on the magnetic stand. Do not over dry.
    11. Remove tubes from magnet and pipette 30 µL of DNA Suspension Buffer to each sample tube.
    12. Pulse vortex each tube to resuspend the beads into the solution and spin the tubes down. Use P200 pipette to resuspend beads stuck to the side of the tube.
    13. Incubate at RT for 2-5 minutes.
    14. Return the tubes to the DynaMag 2 magnetic stand and incubate at RT until clarified (~3 minutes).
    15. Aspirate the 25 µL eluents and transfer to a new 0.2 mL 12-Strip PCR Tube with the sample number for each sample. Discard the 1.5 mL microcentrifuge tubes.
  D. Sample Storage
    1. Samples can be stored at −20° C.±5° C. if downstream application are to be performed at a later date, or at +2° C. to +8° C. if downstream application are to be performed within 24 hours.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A kit comprising a solution comprising a chelating agent, an ionic detergent, a non-ionic detergent, a salt, a cationic polymer, a pH buffering agent, a crowding agent, and paramagnetic beads in a container configured for nucleic acid extraction.

2. The kit of claim 1, wherein the chelating agent comprises one or more selected from the group consisting of enterobactin, deferasirox (DFS), deferiprone (DFP), deferoxamine mesylate, EDTA, and EGTA.

3. The kit of claim 1, wherein the chelating agent is present in an amount between 10-100 mM or between 25-750 μM in the solution.

4. The kit of claim 1, wherein the detergent comprises one or more selected from the group consisting of cholate, deoxycholate, sodium dodecyl sulfate, sarkosyl, n-Dodecyl-β-D-maltoside (DDM), digitonin, NP-40, Triton X-100, Tween 20, and Tween 80.

5. The kit of claim 4, wherein the detergent is present in an amount between 0.1-10% weight/volume of the solution.

6. The kit of claim 1, wherein the salt is present in the amount of 1-2M in solution.

7. The kit of claim 1, wherein the cationic polymer comprises one or more selected from the group consisting of Poly-L-Arginine, Poly-D-Lysine, and Poly-L-Lysine.

8. The kit of claim 7, wherein the cationic polymer is present in an amount between 10-100 mg/L in the solution.

9. The kit of claim 1, wherein the buffering agent comprises one or more selected from the group consisting of Citrate, HEPES, Phosphate, and Tris.

10. The kit of claim 9, wherein the buffering agent is present in an amount between 25-250 mM in the solution.

11. The kit of claim 1, wherein the crowding agent comprises on or more selected from the group consisting of ethanol, isopropanol, PEG 4000, PEG6000, and PEG8000.

12. The kit of claim 11, wherein the crowding agent is present in an amount between 10-20% of the solution.

13. The kit of claim 1, further comprising an antimicrobial.

14. The kit of claim 13, wherein the antimicrobial is selected from a group consisting of penicillin, streptomycin, Amphotericin B, and urine Stabilur tablet.

15. The kit of claim 1, wherein the container is configured for the application of a magnetic field to enable the immobilization of the paramagnetic nucleic acid binding beads and subsequent washing or buffer exchange on the beads.

16. The kit of claim 1, wherein the container is amendable to a high throughput accessioning through barcode labels.

17. The kit of claim 1, wherein the container is configured to accept a biological sample from a sampling swab into the solution.

18. The kit of claim 16, wherein the swab is contacted with a subject suspected of being infected with a pathogen.

19. The kit of claim 17, wherein the pathogen is SARS-COV2.

20. The kit of claim 1, wherein the container is a tube.

21. The kit of claim 1, wherein the container is a 48 or 96 well plate.

* * * * *